United States Patent
Han et al.

(10) Patent No.: US 8,816,112 B2
(45) Date of Patent: Aug. 26, 2014

(54) PROCESS FOR MAKING NOVEL CHIRAL PHOSPHORUS LIGANDS

(71) Applicants: Zhengxu Han, Shrewsbury, MA (US); Chris Hugh Senanayake, Brookfield, CT (US)

(72) Inventors: Zhengxu Han, Shrewsbury, MA (US); Chris Hugh Senanayake, Brookfield, CT (US)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 14/079,916

(22) Filed: Nov. 14, 2013

(65) Prior Publication Data

US 2014/0135506 A1  May 15, 2014

Related U.S. Application Data

(60) Provisional application No. 61/726,749, filed on Nov. 15, 2012.

(51) Int. Cl.
*C07F 9/02* (2006.01)
*C07F 9/28* (2006.01)
*C07F 9/50* (2006.01)

(52) U.S. Cl.
USPC ............... 556/19; 556/13; 556/22; 568/12; 568/15

(58) Field of Classification Search
CPC ............... C07F 9/02; C07F 9/28; C07F 9/50
USPC ............. 556/13, 19, 22; 568/12, 15
See application file for complete search history.

(56) References Cited

U.S. PATENT DOCUMENTS 5,166,389 A * 11/1992 Juge et al. ............ 558/177
5,767,276 A * 6/1998 Zhang ..................... 546/2
8,552,212 B2 10/2013 Qu et al.

OTHER PUBLICATIONS

Bauduin, C. et al., "Highly Enantiomerically Enriched Chlorophosphine Boranes: Synthesis and Applications as P-Chirogenic Electrophilic Blocks." Journal of Organic Chemistry, 2003, vol. 68, pp. 4293-4301.
International Search Report and Written Opinion for PCT/US2013/070025 mailed on Jan. 31, 2014.

* cited by examiner

*Primary Examiner* — Golam M M Shameem
(74) *Attorney, Agent, or Firm* — Michael P. Morris; David L. Kershner

(57) ABSTRACT

Disclosed are methods for making chiral phosphorus ligands including chiral phosphines, chiral phosphine oxides, phosphonamides, and aminophosphines. The chiral phosphorus ligands prepared by the methods of the invention are useful as components of chiral catalysts, e.g., transition metal complexes.

20 Claims, No Drawings

PROCESS FOR MAKING NOVEL CHIRAL PHOSPHORUS LIGANDS

FIELD OF THE INVENTION

The invention relates to methods for making chiral phosphorus ligands including chiral phosphines, chiral phosphine oxides, phosphonamides, and aminophosphines. The chiral phosphorus ligands prepared by the methods of the invention are useful as components of chiral catalysts, e.g., transition metal complexes.

BACKGROUND OF THE INVENTION

Chiral phosphine ligands have been widely used as components of transition metal catalyts, which catalysts are useful for carrying out asymmetric synthesis. Although many methods for making chiral phosphines are known, the chiralities of most of these ligands rely mainly on a chiral substituent group to impart chirality to the resulting phosphine ligand. In contrast, only a limited number of P-chiral ligands have been prepared, presumably because no general and efficient methods are available for their synthesis.

In the 1970s Knowles and coworkers prepared the first prominent P-chiral ligand DIPAMP (see, e.g., reviews by Methot, J. L. et al. *Adv. Synth. Catal.* 2004, 346, 1035-1050; Seayad, J. et al., *Org. Biomol. Chem.* 2005, 3, 719-724; Connon, S. J. *Angew. Chem., Int. Ed.* 2006, 45, 3909-3912; and Benaglia, M. et al. *Org. Biomol. Chem.* 2010, 8, 3824-3830). However, methods for the synthesis of optically active P-chiral phosphines have emerged slowly. Representative methods include the formation and separation of diastereomeric mixtures of menthyl phosphinates, auxiliary-based transformations, enantioselective deprotonation of phosphine-boranes and sulfides, enzymatic resolution, transition metal catalyzed asymmetric phosphine alkylations, dynamic kinetic asymmetric oxidation of racemic phosphines, and through H-menthylphosphinates. Despite these elegant approaches, the currently available methods are often limited in terms of substrate scope and practicality, especially for the synthesis of sterically crowded P-chiral phosphines.

Thus, there is a need to provide a general, practical, and high stereoselective method for the synthesis of P-chiral compounds with diverse structures and functionalities.

BRIEF SUMMARY OF THE INVENTION

In its broadest embodiment, the invention relates to a method of making the compound of formula (I):

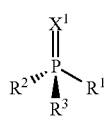

(I)

the method comprising allowing a compound of formula (IIa) or (IIb):

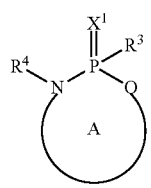

(IIa)

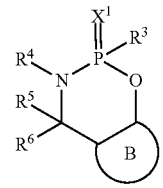

(IIb)

to react with a first organometallic reagent of formula $M^1-R^1$ followed by reaction with a second organometallic reagent of formula $M^2-R^2$ to provide the compound of formula (I); wherein ring A of the compound of formula (IIa) represents a 5- to 7-membered heterocyclic ring optionally substituted by 1 to 3 substituents independently selected from halogen, hydroxyl, —$(C_1-C_6)$alkyl, —$O(C_1-C_6)$alkyl, —$CF_3$, —$(C_6-C_{10})$aryl, and -(5 to 11-membered)heteroaryl;

ring B of the compound of formula (IIb) represents a $(C_6-C_{10})$aryl or a (5 to 11-membered)heteroaryl; wherein each of said $(C_6-C_{10})$aryl and (5 to 11-membered)heteroaryl of said B ring is optionally substituted by 1 to 3 substituents independently selected from halogen, hydroxyl, —$(C_1-C_6)$alkyl, —$O(C_1-C_6)$alkyl, and —$CF_3$;

$R^1$, $R^2$ and $R^3$ represent different groups, wherein;

$R^1$ is selected from —$(C_1-C_6)$alkyl, —$(C_6-C_{10})$aryl, and -(5 to 11-membered)heteroaryl; wherein each of said —$(C_1-C_6)$alkyl, —$(C_6-C_{10})$aryl, and -(5 to 11-membered)heteroaryl of said $R^1$ group is optionally substituted by 1 to 3 substituents independently selected from halogen, hydroxyl, —$(C_1-C_6)$alkyl, —$O(C_1-C_6)$alkyl, —$CF_3$, dioxolanyl, and phenyl optionally substituted with 1 to 3 $R^7$ groups;

each $R^2$ is independently selected from hydrogen, —$(C_1-C_6)$alkyl, —$(C_2-C_6)$alkenyl, —$(C_2-C_6)$alkynyl, —$(C_3-C_6)$cycloalkyl, -(5 to 11-membered)heterocyclyl, —$(C_6-C_{10})$aryl, -(5 to 11-membered)heteroaryl, —$N(R^{2a})_2$, and ferrocenyl; wherein each of said —$(C_1-C_6)$alkyl, —$(C_2-C_6)$alkenyl, —$(C_2-C_6)$alkynyl, —$(C_3-C_6)$cycloalkyl, -(5 to 11-membered)heterocyclyl, —$(C_6-C_{10})$aryl, and -(5 to 11-membered)heteroaryl of said $R^2$ group is optionally substituted by 1 to 3 substituents independently selected from halogen, hydroxyl, —$(C_1-C_6)$alkyl, —$O(C_1-C_6)$alkyl, —$CF_3$, and phenyl optionally substituted with 1 to 3 $R^8$ groups;

each $R^{2a}$ is independently selected from —$(C_1-C_6)$alkyl, —$(C_2-C_6)$alkenyl, —$(C_2-C_6)$alkynyl, —$(C_3-C_6)$cycloalkyl, -(5 to 11-membered)heterocyclyl, —$(C_6-C_{10})$aryl, -(5 to 11-membered)heteroaryl, wherein each of said —$(C_1-C_6)$alkyl, —$(C_2-C_6)$alkenyl, —$(C_2-C_6)$alkynyl, —$(C_3-C_6)$cycloalkyl, -(5 to 11-membered)heterocyclyl, —$(C_6-C_{10})$aryl, and -(5 to 11-membered)heteroaryl of said $R^{2a}$ group is optionally substituted by 1 to 3 substituents independently selected from halogen, hydroxyl, —$(C_1-C_6)$alkyl, —$O(C_1-C_6)$alkyl, —$CF_3$, and phenyl optionally substituted with 1 to 3 $R^8$ groups;

$R^3$ is selected from —$(C_6-C_{10})$aryl, and -(5 to 11-membered)heteroaryl; wherein each of said —$(C_6-C_{10})$aryl, and -(5 to 11-membered)heteroaryl of said $R^3$ group is optionally substituted by 1 to 3 substituents independently selected from halogen, hydroxyl, —$(C_1-C_6)$alkyl, —$O(C_1-C_6)$alkyl, and —$CF_3$, and phenyl optionally substituted with 1 to 3 $R^9$ groups;

$R^4$ is selected from $(C_1-C_6)$alkyl, —$(C_3-C_6)$cycloalkyl, -(5 to 11-membered)heterocyclyl, —$(C_6-C_{10})$aryl, and -(5 to 11-membered)heteroaryl; wherein each of said —$(C_1-C_6)$ alkyl, —(C$_2$-C$_6$)alkenyl, —(C$_2$-C$_6$)alkynyl, —(C$_3$-C$_6$)cycloalkyl, -(5 to 11-membered)heterocyclyl, —(C$_6$-C$_{10}$)aryl, and -(5 to 11-membered)heteroaryl of said R$^4$ group is optionally substituted by 1 to 3 substituents independently selected from halogen, hydroxyl, —(C$_1$-C$_6$)alkyl, —O(C$_1$-C$_6$)alkyl, —CF$_3$, and phenyl, or R$^4$ is selected from phenylsulfonyl, pyridinylsulfonyl, and pyrimidinylsulfonyl; wherein each of said phenylsulfonyl, pyridinylsulfonyl, and pyrimidinylsulfonyl of said R$^4$ group is optionally substituted by 1 to 3 substituents independently selected from halogen, hydroxyl, —(C$_1$-C$_6$)alkyl, —O(C$_1$-C$_6$)alkyl, and —CF$_3$; R$^5$ and R$^6$ are each independently selected from hydrogen, —(C$_1$-C$_6$)alkyl, —CF$_3$, —(C$_3$-C$_6$)cycloalkyl, -(5 to 11-membered)heterocyclyl, —(C$_6$-C$_{10}$)aryl, and -(5 to 11-membered)heteroaryl; wherein each of said —(C$_1$-C$_6$)alkyl, —(C$_3$-C$_6$)cycloalkyl, -(5 to 11-membered)heterocyclyl, —(C$_6$-C$_{10}$)aryl, and -(5 to 11-membered)heteroaryl of said R$^5$ and R$^6$ is optionally substituted by 1 to 3 substituents independently selected from halogen, hydroxyl, —(C$_1$-C$_6$)alkyl, —O(C$_1$-C$_6$)alkyl, and —CF$_3$;

R$^7$, R$^8$ and R$^9$ are each independently selected from —(C$_1$-C$_6$)alkyl, —CF$_3$, —(C$_3$-C$_6$)cycloalkyl, -(5 to 11-membered)heterocyclyl, —(C$_6$-C$_{10}$)aryl, and -(5 to 11-membered)heteroaryl; wherein each of said —(C$_1$-C$_6$)alkyl, —(C$_3$-C$_6$)cycloalkyl, -(5 to 11-membered)heterocyclyl, —(C$_6$-C$_{10}$)aryl, and -(5 to 11-membered)heteroaryl of said R$^7$, R$^8$ and R$^9$ groups are each independently substituted by 1 to 3 groups selected from halogen, hydroxyl, —(C$_1$-C$_6$)alkyl, —O(C$_1$-C$_6$)alkyl, —CF$_3$, and 1,3-dioxolanyl;

X$^1$ is selected from O, S, BH$_3$ or an electron pair;

M$^1$ and M$^2$ are each independently Li, MgX$^2$ or ZnX$^2$;

X$^2$ is selected from F, Cl, Br, and I; and j is 0, 1 or 2.

In a second embodiment (embodiment 2), the invention relates to a method for making the compound of formula (I), wherein X$^1$ is O.

In a third embodiment (embodiment 3), the invention relates to a method for making the compound of formula (I) according to embodiment 1, wherein X$^1$ is an electron pair.

In a fourth embodiment (embodiment 4), the invention relates to a method for making the compound of formula (I) according to any one of embodiments 1 to 3, wherein R$^3$ is phenyl.

In a fifth embodiment (embodiment 5), the invention relates to a method for making the compound of formula (I) according to any one of embodiments 1 to 4, wherein R$^1$ is —(C$_6$-C$_{10}$)aryl; wherein said —(C$_6$-C$_{10}$)aryl is substituted by 1 to 3 substituents independently selected —(C$_1$-C$_6$)alkyl, —O(C$_1$-C$_6$)alkyl, dioxolanyl, and 1,3-dimethoxyphenyl.

In a sixth embodiment (embodiment 6), the invention relates to a method for making the compound of formula (I) according to any of one of embodiments 1 to 4, wherein R$^1$ is —(C$_1$-C$_6$)alkyl.

In a seventh embodiment (embodiment 7), the invention relates to a method for making the compound of formula (I) according to any one of embodiments 1 to 8, wherein R$^2$ is —(C$_1$-C$_6$)alkyl.

In an eighth embodiment (embodiment 8), the invention relates to a method for making the compound of formula (I) according to any one of embodiments 1 to 8, wherein R$^2$ is selected from methyl and t-butyl.

In a ninth embodiment (embodiment 9), the invention relates to a method for making the compound of formula (I) according to any one of embodiments 1 to 6, wherein R$^2$ is ferrocenyl.

In a tenth embodiment (embodiment 10), the invention relates to a method for making the compound of formula (I) according to any one of embodiments 1 to 6, wherein R$^2$ is selected from —(C$_2$-C$_6$)alkenyl and —(C$_2$-C$_6$)alkynyl substituted by phenyl.

In an eleventh embodiment (embodiment 11), the invention relates to a method for making the compound of formula (I) according to any one of embodiments 1 to 6, wherein R$^2$ is selected from phenyl substituted by 1,3-dimethoxyphenyl.

In a twelfth embodiment (embodiment 12), the invention relates to a method for making the compound of formula (I) according to any one of embodiments 1 to 11, wherein R$^4$ is selected from phenylsulfonyl, pyridinylsulfonyl, and pyrimidinylsulfonyl; wherein each of said phenylsulfonyl, pyridinylsulfonyl, and pyrimidinylsulfonyl is optionally substituted by 1 to 3 substituents independently selected from halogen, hydroxyl, —(C$_1$-C$_6$)alkyl, —O(C$_1$-C$_6$)alkyl, and —CF$_3$.

In a thirteenth embodiment (embodiment 13), the invention relates to a method for making the compound of formula (I) according to any of embodiments 1 to 13, wherein the compound of formula (IIa) is reacted with the first organometallic reagent of formula M$^1$-R$^1$ followed by reaction with the second organometallic reagent of formula M$^2$-R$^2$ to provide the compound of formula (I).

In a fourteenth embodiment (embodiment 14), the invention relates to a method for making the compound of formula (I) according to embodiment 13, wherein the compound of formula (IIa) is a five-membered heterocyclic ring optionally substituted by 1 to 3 substituents independently selected from —(C$_1$-C$_6$)alkyl and —(C$_6$-C$_{10}$)aryl.

In a fifteenth embodiment (embodiment 15), the invention relates to a method for making the compound of formula (I) according to any one of embodiments 13 or 14, wherein the compound of formula (IIa) is a five-membered heterocyclic ring substituted by a —(C$_1$-C$_6$)alkyl and phenyl.

In a sixteenth embodiment (embodiment 16), the invention relates to a method for making the compound of formula (I) according to embodiment 13, wherein the compound of formula (IIa) is a five-membered heterocyclic ring of formula:

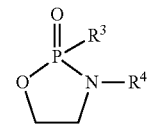

wherein said five-membered heterocyclic ring is optionally substituted by 1 to 3 substituents independently selected from halogen, hydroxyl, —(C$_1$-C$_6$)alkyl, —O(C$_1$-C$_6$)alkyl, —CF$_3$, —(C$_6$-C$_{10}$)aryl, and -(5 to 11-membered)heteroaryl.

In a seventeenth embodiment (embodiment 17), the invention relates to a method for making the compound of formula (I) according to any one of embodiments 13 to 16, wherein the compound of formula (IIa) is a five-membered heterocyclic ring of structure:

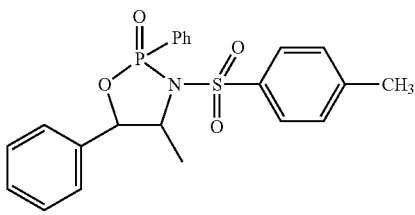 [SMILES: Cc1ccc(S(=O)(=O)N2C(C)C(c3ccccc3)OP2(=O)c2ccccc2)cc1]

including diastereomers and enantiomers thereof.

In an eighteenth embodiment (embodiment 18), the invention relates to a method for making the compound of formula (I) according to any one of embodiments 13 to 17, wherein the compound of formula (IIa) is a five-membered heterocyclic ring of structure:

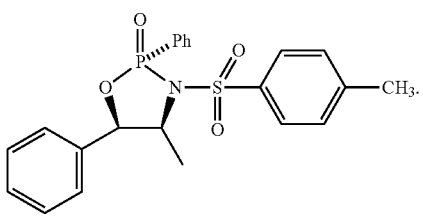 [SMILES: Cc1ccc(S(=O)(=O)N2[C@@H](C)[C@@H](c3ccccc3)O[P@]2(=O)c2ccccc2)cc1]

In a nineteenth embodiment (embodiment 19), the invention relates to a method for making the compound of formula (I) according to any of one of embodiments 1 to 12, wherein the compound of formula (IIb) is reacted with the first organometallic reagent of formula $M^1$-$R^1$ followed by reaction with the second organometallic reagent of formula $M^2$-$R^2$ to provide the compound of formula (I).

In a twentieth embodiment (embodiment 20), the invention relates to a method for making the compound of formula (I) according to embodiment 19, wherein ring B of the compound of formula (IIb) is a —($C_6$-$C_{10}$)aryl optionally substituted by 1 to 3 substituents independently selected from halogen, hydroxyl, —($C_1$-$C_6$)alkyl, —O($C_1$-$C_6$)alkyl, and —$CF_3$.

In a twenty first embodiment (embodiment 21), the invention relates to a method for making the compound of formula (I) according to embodiment 19 or 20, wherein ring B of the compound of formula (IIb) is a $C_6$-aryl optionally substituted by 1 to 3 substituents independently selected from halogen, hydroxyl, —($C_1$-$C_6$)alkyl, —O($C_1$-$C_6$)alkyl, and —$CF_3$.

In a twenty second embodiment (embodiment 22), the invention relates to a method for making the compound of formula (I) according to embodiment 19, 20, or 21, wherein ring B of the compound of formula (IIb) is a $C_6$-aryl substituted by halo.

In a twenty third embodiment (embodiment 23), the invention relates to a method for making the compound of formula (I) according to any one of embodiments 19 to 22, wherein the compound of formula (IIb) is:

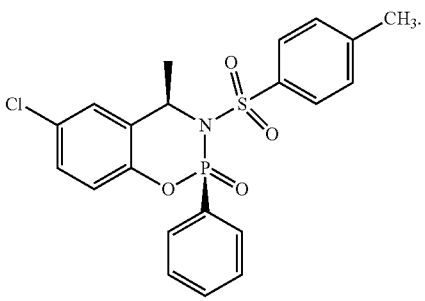 [SMILES: Cc1ccc(S(=O)(=O)N2[C@H](C)c3cc(Cl)ccc3O[P@]2(=O)c2ccccc2)cc1]

DETAILED DESCRIPTION OF THE INVENTION

As noted above, the invention relates to methods of making compounds of formula (I), comprising allowing a compound of formula (IIa) or (IIb) to react with a first organometallic reagent of formula $M^1$-$R^1$ followed by reaction with a second organometallic reagent of formula $M^2$-$R^2$ to provide the compound of formula (I).

Unless otherwise defined herein, the compounds of formula (IIa) and (IIb) including diastereomers and enantiomers thereof.

For all compounds of the invention disclosed hereinabove in this application, in the event the nomenclature is in conflict with the structure, it shall be understood that the compound is defined by the structure.

Abbreviations:
EtOAc=ethyl acetate
Fc=ferrocenyl
isoPrMgCl=isopropylmagnesiumbromide
MeMgBr=methylmagnesiumbromide
MeO-BIBOP=3,3'-di-tert-butyl-4,4'-dimethoxy-2,2',3,3'-tetrahydro-2,2'-bibenzo[d][1,3]oxaphosphole
2-MeO-PhMgB=2-methoxyphenylmagnesiumbromide
PhMgBr=phenylmagnesiumbromide
t-BuLi=tert-butyllithium
t-BuMgCl tert-butylmagnesiumbromide
Ts=4-methylphenylsulfonyl All terms as used herein in this specification, unless otherwise stated, shall be understood in their ordinary meaning as known in the art. For example, "$C_{1-6}$ alkoxy" or "O($C_{1-6}$)alkyl" is a ($C_{1-6}$)alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O).

The term "($C_1$-$C_6$)alkyl" refers to branched and unbranched alkyl groups having from 1 to 6 carbon atoms. Examples of —($C_1$-$C_6$)alkyls include methyl, ethyl, n-propyl, isopropyl, n-butyl, sec-butyl, isobutyl, tert-butyl, n-pentane, iso-pentyl, neopentyl, n-hexane, iso-hexanes (e.g., 2-methylpentyl, 3-methylpentyl, 2,3-dimethylbutyl, and 2,2-dimethylbutyl). It will be understood that any chemically feasible carbon atom of the ($C_1$-$C_6$)alkyl group can be the point of attachment to another group or moiety.

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "($C_3$-$C_6$)cycloalkyl" refers to a stable nonaromatic 3-6 membered monocyclic carbocyclic radical including cyclopropane, cyclobutane, cyclopentane, and cyclohexane.

The term "($C_{6-10}$)aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl. The term "$C_6$-aryl" refers to benzene.

The term "(5 to 11-membered)heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0] hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro [3,4]octanyl, and 7-aza-spiro[3,4]octanyl.

The term "(5 to 11-membered)heteroaryl" refers to an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

It will be understood that one to three carbon ring moieties in the each of the ($C_3$-$C_6$)cycloalkyl and (5 to 11-membered) heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=$NR^2$)—, respectively, where $R^2$ is as defined above.

The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —$CH_2CHF_2$, —$CF_3$ etc.

Each alkyl, cycloalkyl heterocycle or heteroaryl, or the analogs thereof, described herein shall be understood to be optionally partially or fully halogenated.

The chiral phosphine oxides prepared by the methods of the invention are useful intermediates for making chiral phosphine ligands. For example, the chiral phosphine ligand MeO-BIBOP can be prepared from compound 6q as depicted below in Scheme 1 according to known procedures. (See (a) Tang, W.; Qu, B.; Capacci, A. G.; Rodriguez, S.; Wei, X.-T.; Haddad, N.; Narayana, B.; Ma, S.; Grinberg, N.; Yee, N. K.; Krishnamurthy, D.; Senanayake, C. H. *Org. Lett.* 2010, 12, 176-179. (b) Rodriguez, S.; Qu, B.; Haddad, N.; Reeves, D. C.; Tang, W.; Lee, H.; Krishnamurthy, D.; Senanayake, C. H. *Adv. Synth. Catal.* 2011, 353, 533-537. (c) Tang, W.; Keshipeddy, S.; Zhang, Y.; Wei, X.; Savoie, J.; Patel, N. D.; Yee, N. K.; Senanayake, C. H. *Org. Lett.*, 2011, 13, 1366-1369).

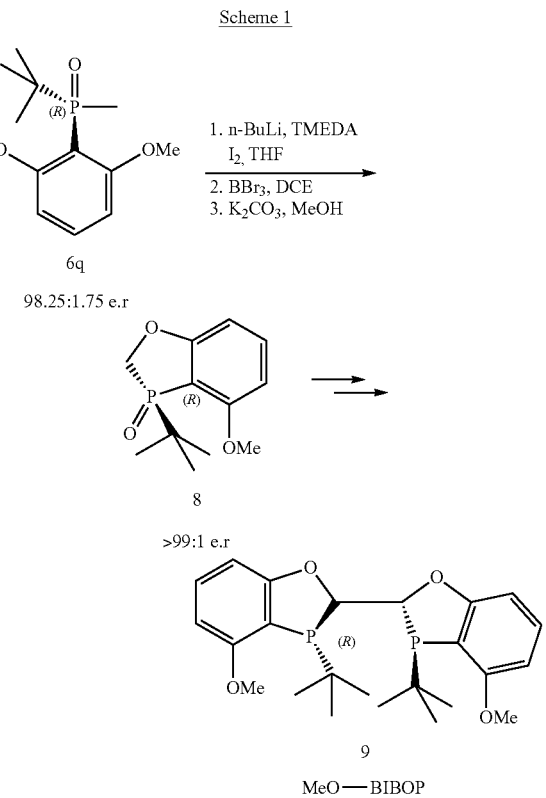

Scheme 1

General Synthetic Methods

Schemes 2 and 3 below each depict a process for making the compound of formula (I) according to the process of the invention.

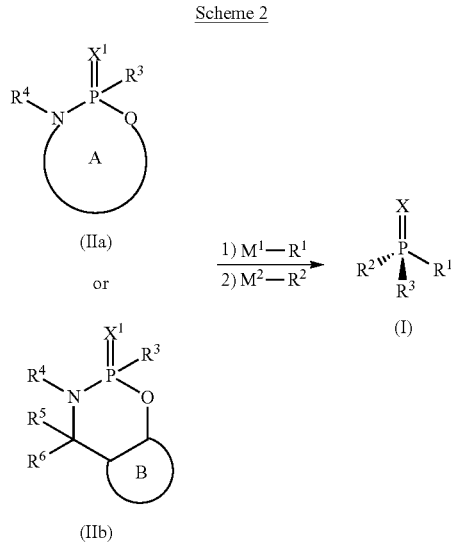

Scheme 2

As depicted in Scheme 2, the compound of formula (IIa) or (IIb) is allowed to react with the compound of formula $M^1$-$R^1$ to form a first intermediate (not shown), which is then allowed to react with the compound with the compound of formula $M^2-R^2$ to provide the compound of formula (I). Typically, the first intermediate can be either not isolated or isolated prior to reaction with the compound of formula $M^2-R^2$. Nonlimiting of compounds of formula $M^1-R^1$ and $M^2-R^2$ useful for making the compound of formula (I) include organolithium reagents and Grignard reagents. Nonlimiting examples of organolithium reagents include PhLi, t-BuLi, MeLi, isoPrLi, 2-MeO-PhLi, CH2-CHLi, and Ph—CCLi. Nonlimiting examples of Grignard reagents include PhMgBr, t-BuMgCl, MeMgBr, isoPrMgCl, and 2-MeO-PhMgBr. Organolithium and Grignard reagents are commercially available or can be prepared by known methods. The reaction depicted in Scheme 2 is carried out in anhydrous, aprotic solvent, such as THF, methylene chloride, ethyl acetate, etc. and under inert atmosphere (e.g., $N_2$, He, Ar).

The compound of formula (IIa) can be prepared according to the process depicted below in Scheme 3.

Scheme 3

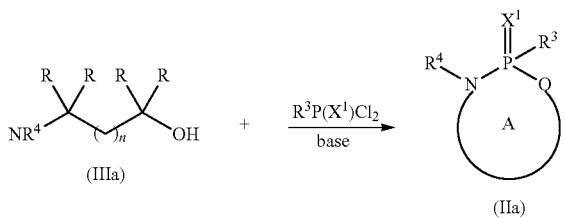

(IIIa)

(IIa)

As depicted in Scheme 3 above, the compound of formula (IIa) is allowed to react with a phosphorus compound of formula $R^3P(X)Cl_2$ in the presence of base, such as pyridine and its derivatives, triethylamine and its derivatives, imidazole and its derivatives, and others to provide the compound of formula (IIa). The R groups depicted in Scheme 3 for the compound of formula (IIa) represent the optional substituents of ring A as defined above, and n is an integer from 0 to 2.

The compound of formula (IIb) can be prepared by the method depicted below in Scheme 4.

Scheme 4

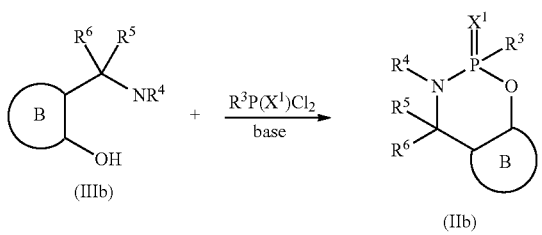

(IIIb)

(IIb)

Compounds of formula (IIb) and $R^3P(X^1)Cl_2$ are commercially available or can be prepared by known methods.

The method for making the compound of formula (IIb) depicted in Scheme 4 above is carried out in a manner similar to that described above for making the compound of formula (IIa) except that the compound of formula (IIb) is used instead of the compound of formula (IIb). Compounds of formula (IIb) are commercially available or can be prepared by known methods.

EXPERIMENTAL

Methods of making the compound of formula (I) using compounds of formula (IIb) are described in Examples 1-17 below.

Step 1: Preparation of Cyclic Intermediates

Scheme 5 below shows a nonlimiting method for making a cyclic intermediate (Intermediate 2) which corresponds to the compound of formula (IIb) described above.

Scheme 5:

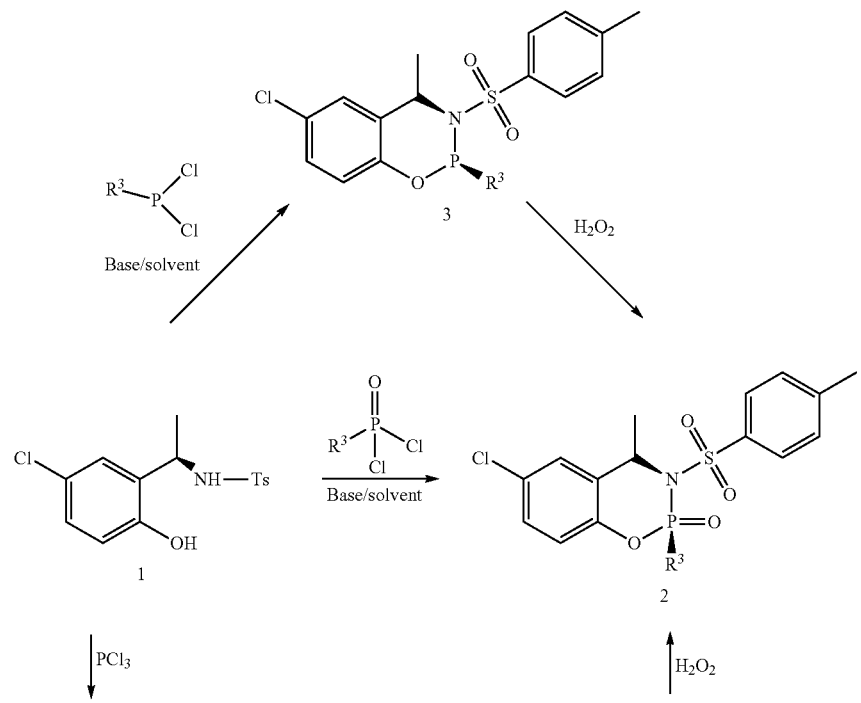

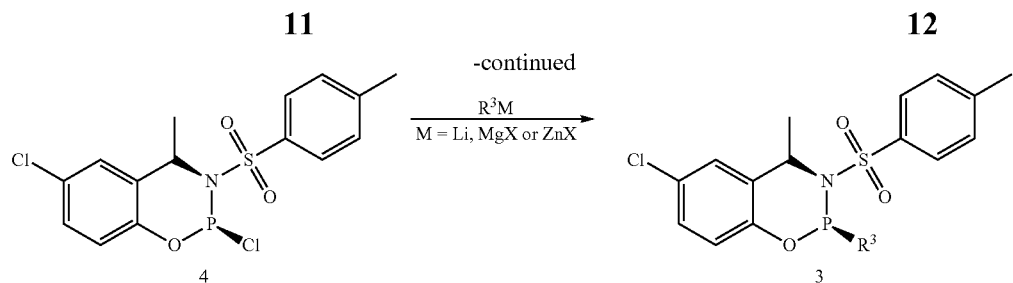

As depicted in Scheme 5, intermediate 2 can be prepared by reacting of compound 1 with O=PCl$_2$R in the presence of base. Intermediate 2 can also be prepared by reacting compound 3 followed with hydrogen peroxide. Compound 3 can be prepared by reacting 1 with PCl$_2$R. Alternatively, 3 can be prepared by reacting 1 with PCl$_3$ to provide compound 4, and reacting 3 with an organometallic reagent (e.g., LiR$^3$, MgR$^1$, or ZnX) to provide 2 (where X is chloro, bromo or iodo).

The methods depicted above in Scheme 5 can be used to prepare specific compounds of formula (IIb) (compounds 2a-2d) shown in Table 2 and Scheme 6 below.

Scheme 6

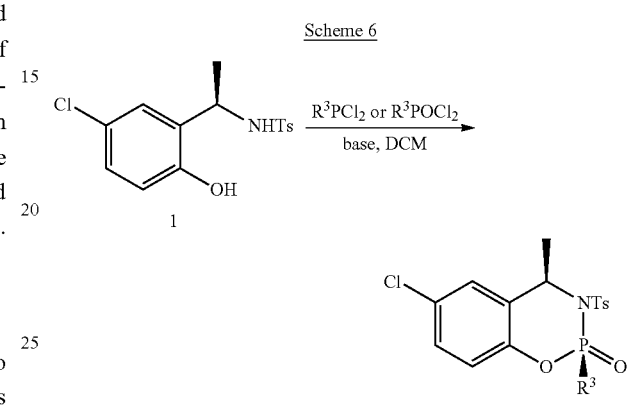

TABLE 1

| | | | Synthesis of 2 | | |
|---|---|---|---|---|---|
| Entry | R$^3$ | Base | Product | yield | dr |
| 1 | 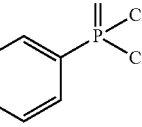 | 1-methyl-imidazole | 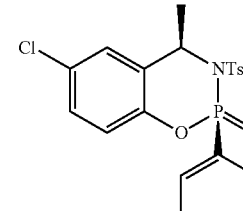 2a | 75% | >99% |
| 2 | 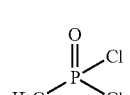 | DMAP | 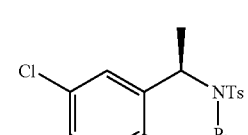 2b | 78% | >99% |
| 3 | 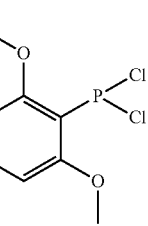 and then H$_2$O$_2$ | Pyridine | 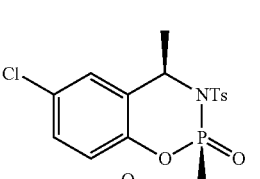 2c | 75% | >99% |

Synthesis of Intermediate 2a

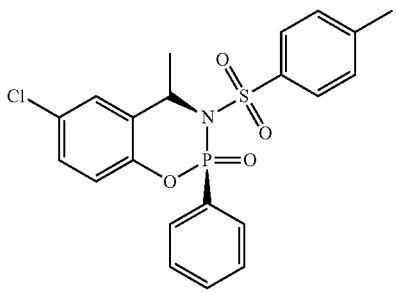

A solution of (R)—N-(1-(5-chloro-2-hydroxyphenyl) ethyl)-4-methylbenzenesulfonamide (1, 100.0 g, 307.69 mmol) in anhydrous dichloromethane (1200 ml) is cooled to −10° C. and then phenyl phosphonic dichloride (57.55 ml, 369.23 mmol, 90% by wt), is added to the reaction mixture. Then 1-methyl imidazole (61.02 ml, 769.2 mmol) is added over 30 minutes while maintaining reaction temperature <−5° C. under argon atmosphere. After completion of the reaction, water (500 mL) is added to reaction mixture to quench the reaction. The phases are separated and the organic phase is washed with 400 ml of 1N HCl followed by 100 ml of water and then 200 ml of saturated sodium bicarbonate solution. The organic phase is then filtered through Celite and then is concentrated. The residue is recrystallized using EtOAc:Hexane (500 ml: 1200 ml) to get 2a (103 g, 75%) as a white solid. $^1$H NMR (400 MHz, CDCl$_3$) δ 1.3 (d, J=7.1 Hz, 3H), 2.29 (s, 3H), 3.8 (s, 3H), 4.58-4.67 (m, 1H), 6.06 (d, J=9.0 Hz, 1H), 6.76 (d, J=2.7 Hz, 1H), 6.88 (dd, J=2.8, 8.7 Hz, 1H), 6.95-7.02 (m, 3H), 7.09-7.18 (m, 2H), 7.43-7.51 (m, 4H), 7.54-7.63 (m, 2H), 7.88-7.95 (m, 2H), 8.1 (ddd, J=1.5, 7.6 Hz, 1H). $^{13}$C NMR (100 MHz, CDCl$_3$) δ 21.7, 24.5, 56.1, 121.7 (d, J=4.7 Hz), 125.8 (d, J=1.5 Hz), 127.5, 128.3, 128.7, 128.9, 129.4, 129.8 (d, J=2.6 Hz), 130.5, 131.5, 131.6, 132.2 (d, J=11.8 Hz), 133.4 (d, J=3.4 Hz), 135.2, 144.9, 145.7 (d, J=8.9 Hz). $^{31}$P NMR (162 MHz, CDCl$_3$) δ 13.530.

Synthesis of Intermediate 2b

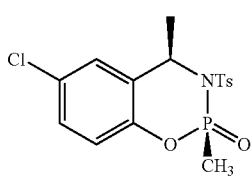

A solution of (R)—N-(1-(5-chloro-2-hydroxyphenyl) ethyl)-4-methylbenzenesulfonamide (1, 100.0 g, 307.69 mmol) in anhydrous dichloromethane (800 ml) is cooled to −10° C. and then methyl phosphonic dichloride (61.19 g., 460.38 mmol) is added to the reaction mixture. Then 4-N,N-dimethyl-pyridine (DMAP) (78.7 g., 644.53 mmol) is added over 30 minutes while maintaining the temperature <−10° C. under argon atmosphere. Then the mixture is stirred at 0° C. for about 2 h to complete the reaction. The reaction mixture is quenched by adding 400 ml of water and the aqueous phase is extracted once with methylene chloride. The combined organic phase organic phases were washed with 350 ml of 1N HCl. The organic phase is then filtered through Celite and concentrated. The residue is recrystallized using isopropanol:water to get 2b (92 g, 78% yield) as a white solid. $^1$H NMR (400 MHz, CDCl$_3$) δ 1.67 (d, J=76.8 Hz, 3H), 2.29 (d, J=17.9 Hz, 3H), 2.38 (s, 3H), 4.47-4.57 (m, 1H), 6.86 (d, J=2.5 Hz, 1H), 7.01 (dd, J=1.1, 8.6 Hz, 1H), 7.2 (dd, J=2.4, 8.5 Hz, 1H), 7.24 (s, 1H), 7.26 (s, 1H), 7.95 (dd, J=1.8, 5.8 Hz, 2H). $^{13}$C NMR (100 MHz, CDCl$_3$) δ 17.2, 18.5, 21.5, 23.5, 55.7, 121.2 (d, J=4.2 Hz), 125.8 (d, J=1.5 Hz), 127.9, 129.7, 129.8, 130.2 (d, J=1.7 Hz), 131.6 (d, J=8.1 Hz), 135.5, 144.7, 145.2 (d, J=9.4 Hz). $^{31}$P NMR (162 MHz, CDCl$_3$) δ 24.37

Synthesis of Intermediate 2c

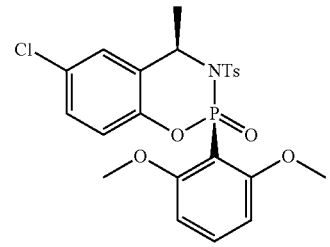

A solution of 1 (19.57 g, 60.24 mmol) in anhydrous dichloromethane (220 ml) is cooled to −20° C. and then dimethoxy phosphine dichloride (14.40 g., 60.24 mmol) is added to the reaction mixture. Then pyridine (10.48 ml, 79.10 mmol) is added over 30 minutes while maintaining the reaction temperature <−10° C. under argon atmosphere. After addition, the reaction mixture is brought to room temperature and the mixture is stirred at for 2-3 hours and then cooled it to <0° C. Water (100 mL) is added to quench the reaction. The aqueous is removed and the organic phase is washed with 100 ml of 1N HCl and 50 ml of NaHCO$_3$. And to the organic phase H$_2$O$_2$ (7.65 mmol, 78.20 mmol) is added and stirred for another 3 hours. The organic phase is washed using brine and the organic phase is concentrated. The residue is purified on column to yield 2c (23 g, 75% yield) as a white solid. $^1$H NMR (400 MHz, CDCl$_3$) δ 1.59 (d, J=7.0 Hz, 3H), 2.36 (s, 3H), 3.98 (s, 6H), 4.58-4.68 (m, 1H), 6.62-6.67 (m, 1H), 6.75 (d, J=2.5 Hz, 1H), 7.05-7.08 (m, 1H), 7.14-7.15 (m, 1H), 7.20 (d, J=8.4 Hz, 2H), 7.48 (t, J=8.5 Hz, 1H), 8.04 (d, J=8.4 Hz, 2H). $^{31}$P NMR (400 MHz, CDCl$_3$) δ 7.220

Step 1: Preparation of Ring-opened Intermediates

Cyclic intermediate 2 can be reacted with an organometallic reagent to provide the ring-opened intermediate 5 as shown in Table 2 below.

Scheme 7

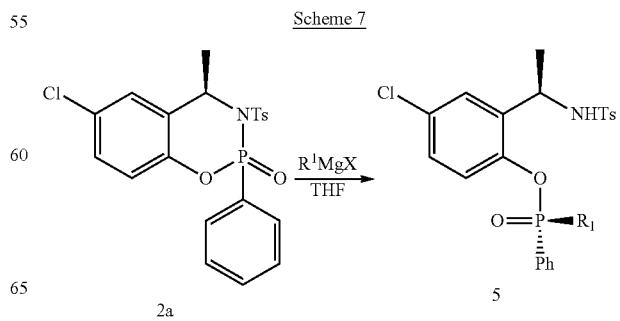

TABLE 2

Synthesis of intermediate 5

| Entry | R¹MgX | product/yield | dr |
|---|---|---|---|
| 1 | 2-methoxyphenyl MgBr | 5a/91% | >99:1 |
| 2 | 2-(1,3-dioxolan-2-yl)phenyl MgBr | 5b/72% | >99:1 |
| 3 | t-BuLi | 5c/65% | >99:1 |
| 4 | mesityl MgBr + LiCl, Dioxane | 5d/52% | >99:1 |
| 5, 6 | 2',6'-dimethoxybiphenyl-2-yl Li | 5e/85% | >99:1 |

Cyclic intermediate 2a can be reacted with an organometallic reagent to provide the ring-opened intermediates 5a-5d as described below.

Synthesis of (R)-4-chloro-2-((S)-1-(4-methylphenylsulfonamido)ethyl)phenyl 2-methoxyphenyl(phenyl)phosphinate (5a)

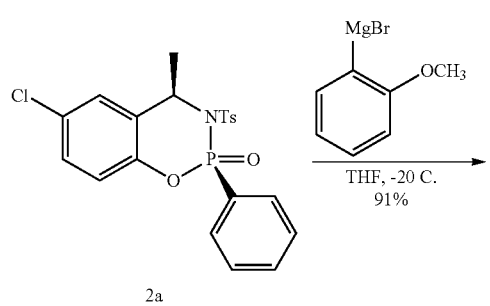

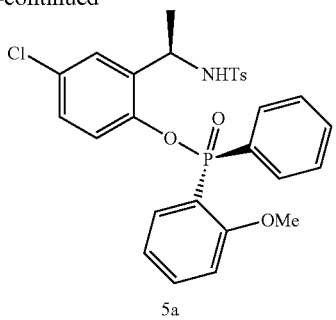

5a

A solution of 2a (4.0 g, 8.93 mmol) in anhydrous THF (40 ml) is cooled to −20° C. under argon atmosphere. And then 2-methoxy phenyl magnesium bromide (9.8 ml, 9.8 mmol, 1.0 M in THF) is added dropwise to the reaction mixture and stirred for 2 hours at −20° C. After the starting material is consumed completely, the reaction mixture is quenched using 10 ml of saturated ammonium chloride solution and diluted with 100 ml of ethyl acetate. The organic layer is dried over sodium sulphate and concentrated. The residue on column eluted with hexane: ethyl acetate, (70:30, v/v) to get 5a as while solid (4.5 g, 91%) in >99:1 dr. $^1$H NMR (400 MHz, CDCl$_3$) δ 1.3 (d, J=7.1 Hz, 3H), 2.29 (s, 3H), 3.8 (s, 3H), 4.58-4.67 (m, 1H), 6.06 (d, J=9.0 Hz, 1H), 6.76 (d, J=2.7 Hz, 1H), 6.88 (dd, J=2.8, 8.7 Hz, 1H), 6.95-7.02 (m, 3H), 7.09-7.18 (m, 2H), 7.43-7.51 (m, 4H), 7.54-7.63 (m, 2H), 7.88=7.95 (m, 2H), 8.1 (ddd, J=1.5, 7.6 Hz, 1H). $^{13}$C NMR (100 MHz, CDCl$_3$) δ 21.4, 22.4, 50.1, 55.9, 111.8 (d, J=7.9 Hz), 117.4, 118.7, 121.0, 121.2, 121.4 (d, J=3.9 Hz), 126.8, 127.8, 128.3 (d, J=5.3 Hz), 128.5, 129.2, 130.9, 131.4, 131.5, 132.3, 132.4 (d, J=2.9 Hz), 134.3 (d, J=6.0 Hz), 135.0 (d, J=7.2 Hz), 135.5 (d, J=1.9 Hz), 137.5, 142.9, 146.9 (d, J=8.5 Hz), 160.6 (d, J=4.6 Hz). $^{31}$P NMR (162 MHz, CDCl$_3$) δ 30.918.

Synthesis of (R)-4-chloro-2-((S)-1-(4-methylphenylsulfonamido)ethyl)phenyl 2-(1,3-dioxolan-2-yl)phenyl(phenyl)phosphinate (5b)

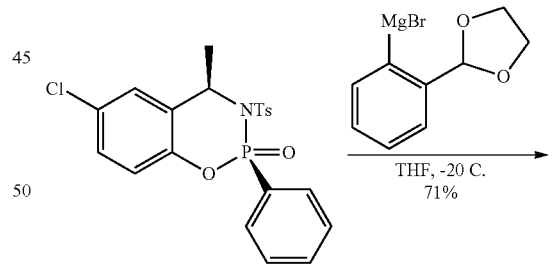

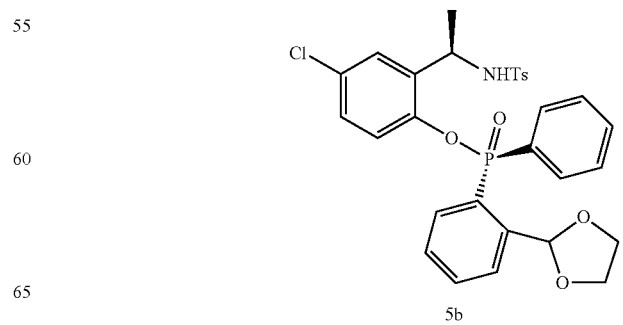

A solution of 2a (10.0 g, 22.32 mmol) in anhydrous THF (80 ml) is cooled to −20° C. under argon atmosphere. And then freshly prepared 2-ethylene diacetal phenyl magnesium bromide (39 ml, 31.24 mmol, 0.8 M in THF) is added dropwise to the reaction mixture and stirred for 2 hours at −20° C. After the starting material is consumed completely, the reaction mixture is quenched using 20 ml of saturated ammonium chloride solution and diluted with 200 ml of ethyl acetate. The organic layer is separated and dried over sodium sulphate and concentrated. The residue is purified on column eluted with 30:70 hexane:ethyl acetate to get 5b as a white solid (9.5 g, 71%) in >99:1 dr. $^1$H NMR (400 MHz, CDCl$_3$) δ 1.19 (d, J=7.1 Hz, 3H), 2.32 (s, 3H), 3.87-3.99 (m, 3H), 4.01-4.10 (m, 1H), 4.74 (q, J=6.8 Hz, 1H), 5.66 (d, J=7.5 Hz, 1H), 6.5 (s, 1H), 6.88-6.93 (m, 2H), 7.02-7.09 (m, 3H), 7.43-7.59 (m, 6H), 7.66 (t, J=7.1 Hz, 1H), 7.74-7.88 (m, 3H), 8.06-8.12 (m, 1H). $^{13}$C NMR (100 MHz, CDCl$_3$) δ 21.4, 22.1, 48.5, 65.1, 65.4, 100.3 (d, J=4.0 Hz), 121.9 (d, J=3.8 Hz), 126.8, 127.7, 127.8, 128.1, 128.6, 128.8, 129.0, 129.2, 129.3, 129.4, 129.8, 131.0, 131.1, 131.2, 132.6 (d, J=2.8 Hz), 133.2 (d, J=6.7 Hz). 137.5, 142.1, 142.2, 143.0, 146.3, 146.4. $^{31}$P NMR (162 MHz, CDCl$_3$) δ 32.271 ppm.

Synthesis of (S)-4-chloro-2-((S)-1-(4-methylphenylsulfonamido)ethyl)phenyl tert-butyl(phenyl)phosphinate (5c)

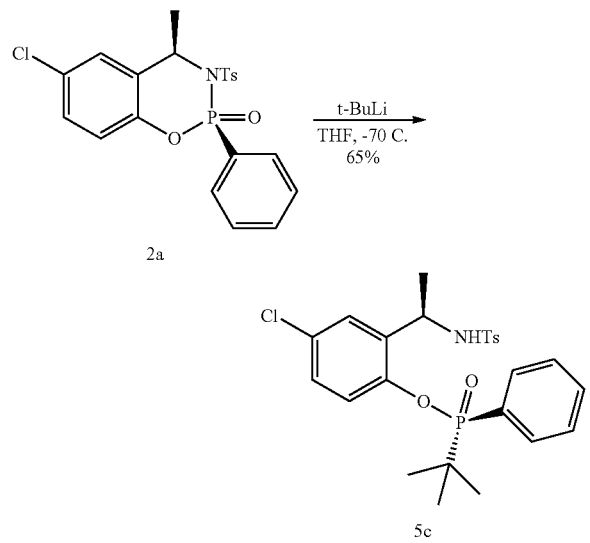

A solution of 2a (5 g, 11.18 mmol) in anhydrous THF (60 ml) is cooled to −70° C. under argon atmosphere. And then t-BuLi (8.3 ml, 13.4 mmol, 1.6 M in pentane) is added dropwise and the mixture is stirred for 1 hour at −70° C. After the starting material is consumed completely, the reaction mixture is quenched using 10 ml of saturated ammonium chloride solution and extracted using 200 ml of ethyl acetate. The organic layer is dried over sodium sulphate and concentrated. The residue is purified on column eluted with 10:90 hexane:ethyl acetate to provide 5c as a white solid (3.6 g, 65%) in >99:1 dr. $^1$H NMR (400 MHz, CDCl$_3$) δ 1.3 (d, J=16.6 Hz, 9H), 1.40 (d, J=6.9 Hz, 3H), 2.31 (s, 3H), 5.05 (q, J=7.1 Hz, 1H), 6.03 (d, J=7.8 Hz, 1H), 6.8 (dd, J=2.6, 8.8 Hz, 1H), 7.01-7.12 (m, 4H), 7.43-7.50 (m, 2H), 7.54-7.60 (m, 3H), 7.72-7.80 (m, 2H). $^{13}$C NMR (100 MHz, CDCl$_3$) δ 21.4, 23.3, 24.2, 33.3, 34.3, 47.3, 120.6 (d, J=4.4 Hz), 126.8, 127.2, 127.7, 128.0, 128.5, 128.6, 129.1, 129.4, 132.7 (d, J=2.6 Hz), 132.9, 133.0, 133.9 (d, J=6.1 Hz), 137.2, 143.2, 146.8 (d, J=9.6 Hz). $^{31}$P NMR (162 MHz, CDCl$_3$) δ 50.882 ppm.

Synthesis of (R)-4-chloro-2-((S)-1-(4-methylphenylsulfonamido)ethyl)phenyl mesityl(phenyl)phosphinate (5d)

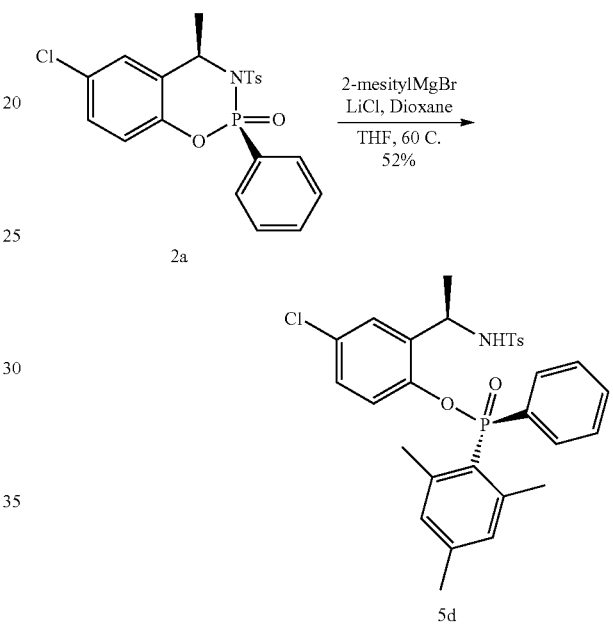

A solution of 2-mesityl magnesium bromide (24.1 ml, 24.1 mmol, 1.0 M in THF), Lithium chloride (48.3 ml, 24.1 mmol, 0.5 M in THF) and dioxane (2.36 ml, 26.8 mmol) are mixed together and heated at 45° C. for 1 hour and then the mixture is brought to room temperature and then 2a (4 g, 8.94 mmol) dissolved in 30 ml THF is added to this reaction flask dropwise. After addition, the mixture warmed to 60° C. and stirred for 6 hours. The reaction is quenched using 10 ml of ammonium chloride saturated solution and the mixture is extracted using 100 ml of ethyl acetate. The organic layer is dried over sodium sulphate and concentrated. The residue is purified on column to yield 5d as a white solid (2.6 g, 52%) in >99:1 dr. $^1$H NMR (400 MHz, CDCl$_3$) δ 1.39 (d, J=6.9 Hz, 3H), 2.32 (s, 3H), 2.34 (s, 3H), 2.50 (s, 3H), 4.74 (q, J=7.3 Hz, 1H), 5.87 (d, J=7.1 Hz, 1H), 6.66-6.69 (m, 1H), 6.85-6.90 (m, 2H), 6.98 (d, J=4.1 Hz, 2H), 7.04 (d, J=7.9 Hz, 2H), 7.42-7.50 (m, 2H), 7.53-7.59 (m, 3H), 7.6-7.81 (m, 2H). $^{13}$C NMR (100 MHz, CDCl$_3$) δ 21.2 (d, J=1.4 Hz), 21.4, 22.8, 23.4 (d, J=3.4 Hz), 48.7, 121.1 (d, J=3.8 Hz), 122.2, 123.4, 126.9, 128.1 (d, J=16.2 Hz), 128.9 (d, J=14.0 Hz), 129.8, 130.2 (d, J=13.2 Hz), 131.3 (d, J=13.4 Hz), 132.3 (d, J=3.0 Hz), 132.7, 134.1, 135.5 (d, J=5.1 Hz), 137.4, 143.0, 143.2 (d, J=3.0 Hz), 143.9, 144.0, 145.8 (d, J=8.3 Hz). $^{31}$P NMR (162 MHz, CDCl$_3$) δ 36.669.

Synthesis of (S)-4-chloro-2-((R)-1-(4-methylphenyl-sulfonamido)ethyl)phenyl ((r)-2',6'-dimethoxybiphenyl-2-yl)(phenyl)phosphinate 5e

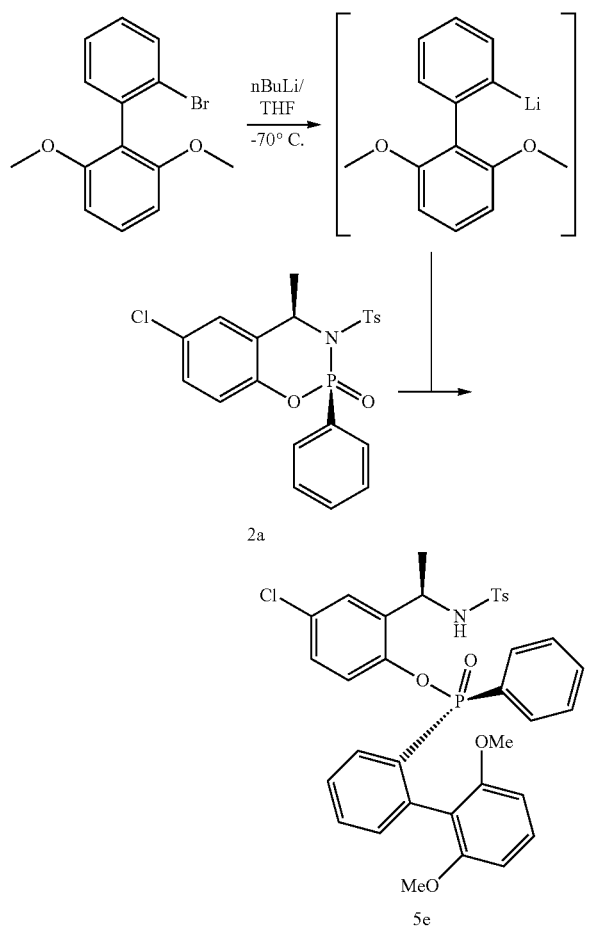

A solution of 2'-bromo-2,6-dimethoxybiphenyl (2 g, 6.83 mmol) in THF (30 mL) was cooled −70° C. and nBuLi (3.5 mL, 2 M in hexane) was added slowly and the mixture was stirred for 2 h at that temperature. Then the mixture was warmed to −20° C. and stirred for 15 min and cooled to −70° C. again. A solution of 2a (2.7 g, 6.03 mmoL) in THF (50 mL) was added dropwise. The reaction mixture was stirred about 2 h at that temperature and warmed to −20° C. and stirred for about 30 min to complete the reaction. Then 10 mL of saturated ammonium chloride solution was added top quench the reaction and the mixture was extracted with 60 mL of ethyl acetate. The organic phase was dried and concentrated. The residue was purified on column eluted with EtOAc/hexane (10:90 to 45:55, v/v) to yield 3.8 g product in 85% yield and >99.5:0.5 er. $^1$H NMR (400 MHz, CDCl$_3$) δ 1.19 (d, J=7.2 Hz, 3H), 2.36 (s, 3H), 3.17 (s, 3H), 3.44(s, 3H), 4.64 (m, 1H), 5.76 (d, J=6.52 Hz, 1H), 6.32 (d, J=8.56 Hz, 2H), 6.75-6.80 (m, 1H), 6.84-6.89 (m, 1H), 6.96-7.00 (m, 1H), 7.01-7.10 (m, 2H), 7.15-7.27 (m, 4H), 7.29-7.37 (m, 2H), 7.37-7.43 (m, 1H), 7.51-7.57 (m, 1H), 7.61-7.70 (m, 3H), 8.28-8.36 (m, 1H). $^{13}$C NMR (100 MHz, CDCl$_3$) δ 21.50, 22.22, 48.44, 54.82, 55.30, 102.79, 103.34, 116.74, 116.78, 122.36, 122.39, 127.12, 127.15, 127.25, 127.69, 127.82, 127.89, 127.92, 129.37, 129.62, 129.73, 129.80. 130.21, 130.97, 131.17, 131.28, 131.51, 131.54, 131.59, 132.68, 132.80, 132.83, 133.36, 133,44, 135.40, 135.45, 137.36, 139.68, 139.81, 143.02, 146.20, 146.28, 157.52, 158.14. $^{31}$P NMR (162 MHz, CDCl$_3$) δ 30.92; HRMS: calculated for C$_{35}$H$_{33}$ClNO$_6$PS (M+H): 662.1533; found: 662.1525.

EXAMPLES 1-7

Scheme 8 below describes a method of making the compounds of the invention by reacting cyclic intermediate 2a with (2-methoxyphenyl)magnesium bromide to provide the compound 5a followed by reaction with a lithium alkyl to provide a compound of the invention (denoted as compound 6).

Scheme 8

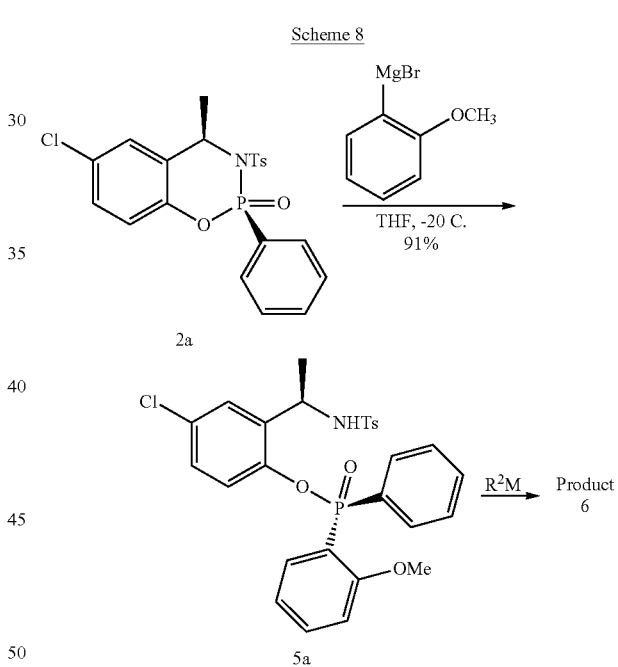

Specific compound of the invention prepared according to Scheme 8 are described in Table 3.

TABLE 3

| Synthesis of compounds of the invention (Ex-1 to Ex-7). | | | | |
|---|---|---|---|---|
| Entry | R$^2$M | Product | er | yield |
| Ex. 1 | MeMgBr | 6a | >99% | 91% |

TABLE 3-continued

Synthesis of compounds of the invention (Ex-1 to Ex-7).

| Entry | R²M | Product | er | yield |
|---|---|---|---|---|
| Ex. 2 | tBuLi | 6b | 97% | 84% |
| Ex. 3 | Fc—Li<br>Fc = Ferrocene | 6c | >99% | 82% |
| Ex. 4 | isopropyl-Li | 6d | >95% | 63% |
| Ex. 5 | vinyl-MgBr | 6e | >98% | 70% |
| Ex. 6 | PhC≡C-Li | 6f | 96% | 54% |
| Ex. 7 | (biaryl-Li) | 6g | 98% | 87% |

Example 1

Synthesis of 6a

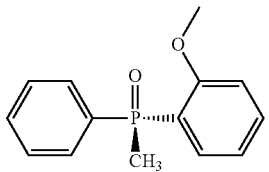 [SMILES: COc1ccccc1[P@@](C)(=O)c1ccccc1]

A solution of (R)-4-chloro-2-((S)-1-(4-methylphenylsulfonamido)ethyl)phenyl 2-methoxyphenyl(phenyl)phosphinate (5a, 0.2 g, 0.359 mmol) in anhydrous THF (5 ml) is cooled to −10° C. under argon atmosphere. Then methyl Grignard reagent (0.47 ml, 1.43 mmol, 3.0 M in THF) is added dropwise to the reaction mixture and stirred for 15 minutes at −10° C. After the starting material is consumed completely, the reaction mixture is quenched using 1 ml of saturated ammonium chloride solution and extracted using 30 ml of ethyl acetate. The organic layer is dried over sodium sulphate and concentrated. The residue is purified on column eluted with 5% MeOH-ethyl acetate mixture to provided 6a (88 mg, 91% yield) in 99.9:0.1 er. $^1$H NMR (400 MHz, CDCl$_3$) δ 2.07 (d, J=14.1 Hz, 3H), 3.72 (s, 3H), 6.86-6.91 (m, 1H), 7.07-7.13 (m, 1H), 7.39-7.53 (m, 4H), 7.71-7.77 (m, 2H), 7.96 (ddd, J=1.8, 7.96 Hz, 1H). $^{13}$C NMR (100 MHz, CDCl$_3$) δ 15.8, 16.5, 55.2, 110.8 (d, J=6.6 Hz), 121.0 (d, J=11.0 Hz), 121.9, 128.2 (d, J=12.1 Hz), 130.2 (d, J=10.2 Hz), 131.2 (d, J=2.8 Hz), 133.8-134.0 (m), 134.5 135.5, 159.9 (d, J=4.9 Hz). $^{31}$P (162 MHz, CDCl$_3$) δ 28.39 ppm. HPLC: Column: Chiralpack AD-H, 4.6×250 mm; IPA: Hexane (12: 88), 1.5 ml/min, 220 nm, r$_t$=10.8 min, 14.5 min

Example 2

Synthesis of 6b

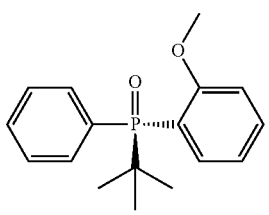 [SMILES: COc1ccccc1[P@@](=O)(c1ccccc1)C(C)(C)C]

A solution of (R)-4-chloro-2-((S)-1-(4-methylphenylsulfonamido)ethyl)phenyl 2-methoxyphenyl(phenyl)phosphinate (5a, 0.250 g, 0.450 mmol) in anhydrous THF (5 ml) is cooled to −70° C. under argon atmosphere. Then t-BuLi (1.2 ml, 1.8 mmol, 1.6 M in pentane) is added dropwise to the reaction mixture and stirred for 30 minutes at −70° C. After the starting material is consumed completely, the reaction mixture is quenched using 2 ml of saturated ammonium chloride solution and extracted using 30 ml of ethyl acetate. The organic layer is dried over sodium sulphate and concentrated. The residue is purified on column eluted with 5% MeOH-ethyl acetate mixture to get 6b (108 mg, 83%) in 98.7:1.3 er. $^1$H NMR (100 MHz, CDCl$_3$) δ 1.26 (d, J=15.5 Hz, 9H), 3.7 (s, 3H), 6.81-6.93 (m, 1H), 7.1 (t, J=7.2 Hz, 1H), 7.37-7.57 (m, 4H), 7.91-7.97 (m, 2H), 8.17 (ddd, J=1.6, 7.5 Hz). $^{13}$C NMR (100 MHz, CDCl$_3$) δ 25.9 (d, J=1.0 Hz), 35.3, 35.1, 54.6, 110.8 (d, J=6.6 Hz), 119.7, 120.7, 120.9 (d, J=10.1 Hz), 127.8 (d, J=11.4 Hz), 131.0 (d, J=2.8 Hz), 132.0 (d, J=8.9 Hz), 132.5, 133.4, 133.5 (d, J=2.1 Hz), 136.1 (d, J=4.9 Hz), 159.5 (d, J=4.2 Hz). $^{31}$P NMR: (162 MHz, CDCl$_3$) δ 42.686

Chiral HPLC: ChiralpackAD-H, 4.6×250 mm; IPA: Heptane (25:75), 1.2 ml/min, 220 nm, r$_t$=3.7 min and 4.7 min

Example 3

Synthesis of 6c

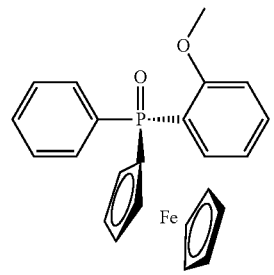

A solution of (R)-4-chloro-2-((S)-1-(4-methylphenylsulfonamido)ethyl)phenyl 2-methoxyphenyl(phenyl)phosphinate (5a, 0.2 g, 0.359 mmol) in anhydrous THF (5 ml) is cooled to −78° C. under argon atmosphere. Then fresh generated ferrocenyl lithium (FcLi) at −78 C. The reaction is completed in 30 minutes. The reaction is quenched using 2 ml of saturated ammonium chloride solution and extracted using 30 ml of ethyl acetate. The organic layer is dried over sodium sulphate and concentrated. The residue is purified on column to provide 6c (123 mg, 82% yield) in 99.7:0.3 er. $^1$H NMR (500 MHz, CDCl$_3$) δ 3.52 (s, 3H), 4.13 (s, 5H), 4.44 (s, 2H), 4.47 (s, 1H), 4.59 (s, 1H), 6.85-6.90 (m, 1H), 7.10 (t, J=7.6 Hz, 1H), 7.35-7.40 (m, 1H), 7.41-7.46 (m, 1H), 7.50 (t, J=7.27 Hz, 1H), 7.64-7.70 (m, 1H), 7.96 (ddd, J=1.8 Hz, 7.5 Hz, 1H). $^{13}$C NMR (125 MHz, CDCl$_3$) δ 55.2, 69.5, 69.6, 70.9, 71.0, 71.2, 72.1, 72.2, 72.6, 72.8, 72.9, 73.6, 111.5 (d, J=6.4 Hz), 120.6 (d, J=11.4 Hz), 122.5, 123.3, 127.7, 127.8, 130.8, 130.8, 130.9, 133.6 (d, J=1.9 Hz), 134.3, 134.4, 135.4, 136.3, 160.3 (d, J=3.8 Hz). $^{31}$P NMR (300 MHz, CDCl$_3$) δ 26.948 ppm.

HPLC: ChiralpackAD-H, 4.6×250 mm; IPA: Heptane (25: 75); 1.2 ml/min; 230 nm, r$_t$=10.2, 10.9 min

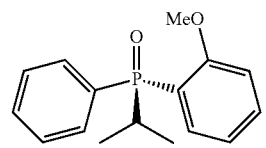 [SMILES: COc1ccccc1[P@@](=O)(c1ccccc1)C(C)C]

Example 4

Synthesis of 6d

A solution of (R)-4-chloro-2-((S)-1-(4-methylphenylsulfonamido)ethyl)phenyl 2-methoxyphenyl(phenyl)phosphinate (5a, 0.2 g, 0.359 mmol) in anhydrous THF (5 ml) is cooled to −70° C. under argon atmosphere. And then isopropyl-Li (1.52 ml, 1.07 mmol, 0.7 M in pentane) is added dropwise to the reaction mixture and stirred for 30 minutes at −70° C. After the starting material is consumed completely, the reaction is quenched using 2 ml of saturated ammonium chloride solution and then it is extracted using 30 ml of ethyl acetate. The organic layer is dried over sodium sulphate and concentrated. The residue purified on column eluted with 5% MeOH-ethyl acetate to provide 6d (62 mg, 63%) in 99:1 er. $^1$H NMR (400 MHz, CD$_3$OD) δ 0.94-1.07 (m, 6H), 2.87-2.96 (m, 1H), 3.85 (s, 3H), 7.06-7.13 (m, 2H), 7.45-7.56 (m, 4H), 7.81-7.90 (m, 3H). $^{13}$C NMR (100 MHz, CD$_3$OD) δ 14.6 (d, J=3.1 Hz), 14.9 (d, J=2.8 Hz), 24.7, 25.5, 55.3, 111.3 (d, J=6.7 Hz), 120.0, 120.8 (d, J=10.3 Hz), 120.9, 128.2 (d, J=11.3 Hz), 130.7 (d, J=9.2 Hz), 131.2 (d, J=2.7 Hz), 132.9, 133.5 (d, J=4.8 Hz), 133.7 (d, J=2.2 Hz), 133.8, 159.0 (d, J=4.8 Hz). $^{31}$P NMR (162 MHz, CD$_3$OD) δ 35.689 ppm. HPLC: Column: ChiralpackAD-H, 4.6×250 mm; IPA: Heptane (25:75), 1.2 ml/min, 220 nm, r$_t$=4.1 min, 4.8 min.

Example 5

Synthesis of 6e

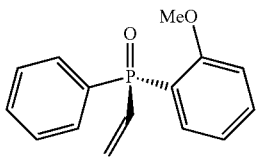 [SMILES: C=C[P@](=O)(c1ccccc1)c1ccccc1OC]

A solution of (R)-4-chloro-2-((S)-1-(4-methylphenylsulfonamido)ethyl)phenyl 2-methoxyphenyl(phenyl)phosphinate (5a, 0.2 g, 0.359 mmol) in anhydrous THF (5 ml) is cooled to −40° C. under argon atmosphere. And then vinyl magnesium chloride (0.78 ml, 1.25 mmol, 1.6 M in THF) is added dropwise to the reaction mixture and stirred for 30 minutes at −40° C. After the starting material consumed, the reaction is quenched with saturated NH4Cl solution and extracted with ethyl acetate. The organic layer is dried over sodium sulphate and concentrated. The residue is purified on column to provide 6e (65 mg, 70% yield) in >99:1 er. $^1$H NMR (400 MHz, CDCl$_3$) δ 3.67 (s, 3H), 6.28 (dd, J=1.8, 12.7 Hz, 1H), 6.50 (dd, J=1.9, 18.7 Hz), 6.79-6.95 (m, 2H), 7.10-7.16 (m, 1H), 7.37-7.55 (m, 4H), 7.62-7.69 (m, 2H), 8.02 (ddd, J=1.8, 7.5 Hz, 1H). $^{13}$C NMR (100 MHz, CDCl$_3$) δ 55.3, 110.9 (d, J=6.8 Hz), 119.6, 120.6, 121.2 (d, J=11.5 Hz), 128.1, 128.2, 128.3, 130.5, 130.6, 130.7, 131.3 (d, J=2.7 Hz), 133.6, 134.0, 134.1, 134.1, 134.2, 134.7, 160.0(d, J=4.1 Hz). $^{31}$P NMR (162 MHz, CDCl$_3$) δ 20.76 ppm. HPLC: Column: ChiralpackAD-H, 4.6×250 mm; Heptane/EtOH (85/15), 1.0 ml/min, 220 nm, r$_t$=7.2 min, 10.3 min.

Example 6

Synthesis of 6f

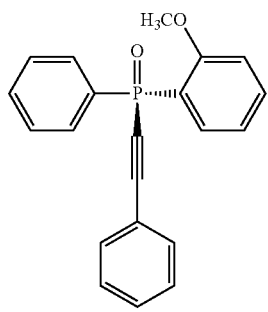 [SMILES: COc1ccccc1[P@](=O)(C#Cc1ccccc1)c1ccccc1]

A solution of (R)-4-chloro-2-((S)-1-(4-methylphenylsulfonamido)ethyl)phenyl 2-methoxyphenyl(phenyl)phosphinate (5a, 0.100 g, 0.179 mmol) in anhydrous THF (5 ml) is cooled to −70° C. under argon atmosphere. And then phenylacetylidine lithium (0.55 ml, 0.537 mmol, 1.0 M in THF) is added dropwise to the reaction mixture and stirred for 30 minutes at −70° C. After the starting material is consumed, the reaction is quenched using 1 ml of saturated ammonium chloride solution and extracted using 30 ml of ethyl acetate. The organic layer is dried over sodium sulphate and concentrated and purified on column to provide 6f (59 mg, 53% yield) in 98.1:1.8 er. $^1$H NMR (400 MHz, CDCl$_3$) δ 3.70 (s, 3H), 6.88-6.93 (m, 1H), 7.09-7.14 (m, 1H), 7.34-7.61 (m, 9H), 7.88-7.96 (m, 2H), 8.07 (ddd, J=1.8 Hz, 7.6 Hz, 1H). $^{13}$C NMR (100 MHz, CDCl$_3$) δ 55.5, 76.7, 84.1, 103.5, 103.8, 111.5 (d, J=7.1 Hz), 120.5, 120.8 (d, J=13.3 Hz), 121.2, 128.0, 128.2, 128.5, 130.3, 130.7, 130.8, 131.6 (d, J=3.1 Hz), 132.4 (d, J=1.8 Hz), 133.8 (d, J=8.0 Hz), 134.5 (d, J=2.0 Hz). $^{31}$P NMR (162 MHz, CDCl$_3$) δ: 5.5 ppm. Chiral HPLC: ChiralpackAD-3, 4.6×150 mm; IPA: Heptane (25:75); 1.5 ml/min, 220 nm, r$_t$=4.1 min and 5.4 min.

Example 7

Synthesis of 6 g

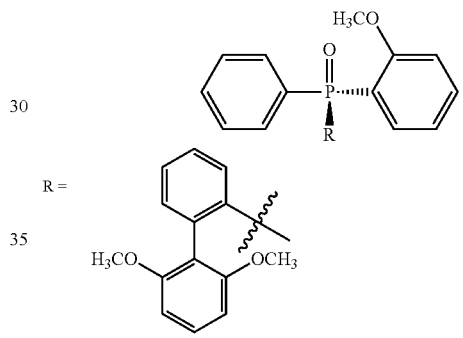

A solution of (R)-4-chloro-2-((S)-1-(4-methylphenylsulfonamido)ethyl)phenyl 2-methoxyphenyl(phenyl)phosphinate (5a, 0.100 g, 0.180 mmol) in anhydrous THF (5 ml) is cooled to −70° C. under argon atmosphere. And in another round bottom flask corresponding biaryl-dimethoxy-Li specie is prepared by reacting biaryl-dimethoxy-bromide (200 mg, 0.684 mmol) with n-butyl lithium (0.27 ml, 0.684 mmol, 2.5 M in hexane), in dry THF at −70° C. for 30 minutes and then warm to −25° C., stirred for 30 minutes and a slurry formed and it is added to the another stirring flask while maintaining the temperature below −70° C. and stirred for 30 minutes. After the starting material is consumed completely, the reaction mixture is quenched using 2 ml of saturated ammonium chloride solution and extracted using 30 ml of ethyl acetate. The organic layer is dried over sodium sulphate and concentrated and purified on column to provide 6 g (68 mg, 87% yield) in 99.2:0.8 er. $^1$H NMR (400 MHz, CDCl$_3$) δ 3.42 (s, 3H), 3.51 (d, J=13.3 Hz, 6H), 6.18 (d, J=8.9 Hz, 1H), 6.26 (d, J=8.2 Hz, 1H), 6.7 (bt, J=7.2 Hz, 1H), 6.8 (t, J=7.0 Hz, 1H), 7.01 (t, J=8.4 Hz, 1H), 7.15-7.21 (m, 1H), 7.23-7.40 (m, 5H), 7.46-7.55(m, 2H), 7.58-7.69 (m, 3H). $^{13}$C NMR (100 MHz, CDCl$_3$) δ 55.0, 55.1, 55.3, 102.9 (d, J=13.4 Hz), 110.8 (d, J=6.7 Hz), 117.7 (d, J=3.9 Hz), 120.4 (d, J=11.6 Hz), 121.4, 122.4, 126.2 (d, J=12.9 Hz), 127.3 (d, J=12.7 Hz), 129.1, 130.5 (d, J=2.9 Hz), 130.8 (d, J=2.7 Hz), 131.9 (d, J=10.6 Hz), 132.3 (d, J=10.2 Hz), 132.6, 133.1 (d, J=1.9 Hz), 133.4, 133.5, 133.7, 134.5, 134.6 (d, J=6.9 Hz), 139.0 (d, J=8.14 Hz), 157.5, 157.8, 160.4 (d, J=3.4 Hz). $^{31}$P NMR (162

MHz, CDCl$_3$) δ 26.041. Chiral HPLC: Chiral AGP, 4.0×150 mm; pH5 buffer MB: ACN; isocratic: 79/21; 1.1 ml/min, 220 nm, r$_t$=5.4 min and 7.6 min.

EXAMPLES 8-10

Scheme 9 below describes a method of making the compounds of then invention by reacting cyclic intermediate 2a with (2-methoxyphenyl)magnesium bromide to provide the compound 5b followed by reaction with a lithium alkyl to provide a compound of the invention (denoted as compound 6).

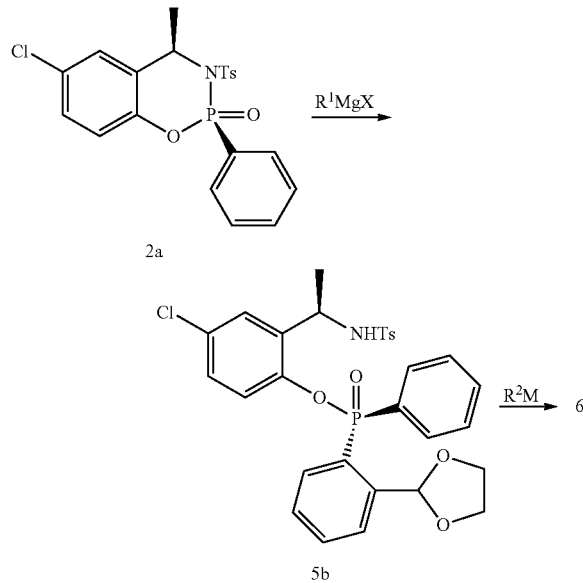

Scheme 9

Specific compounds of the invention prepared according to Scheme 9 are described in Table 4 below.

| Entry | R²M | Product | ee | yield |
|---|---|---|---|---|
| Ex. 8 | CH$_3$MgCl | 6h | >95% | 73% |
| Ex. 9 | t-BuLi | 6i | >80% | 34% |
| Ex. 10 | Fc—Li | 6j | >97% | 82% |

Fc = Ferocene

Example 8

Synthesis of 6h

A solution of (5b, 10.0 g, 16.722 mmol) in anhydrous THF (80 ml) is cooled to −10° C. under argon atmosphere. Methyl Grignard reagent (22 ml, 66.88 mmol, 3.0 M in THF) is added dropwise to the reaction mixture and stirred for 45 minutes at −10° C. After the starting material is consumed, the reaction is quenched using 10 ml of saturated ammonium chloride solution and extracted using 30 ml of ethyl acetate. The organic layer is dried over sodium sulphate and concentrated. The residue is purified on column to provide 6h (3.5 g, 73% yield) in 99:1 er. $^1$H NMR (400 MHz, CDCl$_3$) δ 2.11 (d, J=13.1 Hz, 3H), 3.85-4.07 (m, 4H), 7.37-7.62 (m, 6H), 7.67-7.74 (m, 2H), 7.78-7.83 (m, 1H). $^{13}$C NMR (100 MHz, CDCl$_3$) δ 17.7, 18.4, 65.3, 100.1 (d, J=4.5 Hz), 127.4 (d, J=9.5 Hz), 128.5, 128.6, 128.7, 128.8, 130.5 (d, J=9.9 Hz), 131.7 (d, J=2.8 Hz), 131.8, 131.9, 132.0 (d, J=2.7 Hz), 132.8, 134.3, 135.3, 141.5 (d, J=7.1 Hz). $^{31}$P NMR (162 MHz, CDCl$_3$) δ 32.387 ppm. HPLC: Column: ChiralpackAD-3, 4.6×150 mm; Heptane: EtOH (60:40), 1.0 ml/min, 220 nm, r$_t$=9.2 min, 10.3 min.

Example 9

Synthesis of 6i

A solution of 5b (0.2 g) in THF (5 mL) is cooled -72° C. and t-BuLi (0.6 mL, 1.7 M in heptanes) is added dropwise. The reaction mixture is stirred for 30 min and added 2 mL of ammonium chloride solution to quench the reaction and diluted with EtOAc. The organic is removed and the aqueous phase is extracted with CH$_2$Cl$_2$ The combined organic solvent is concentrated and the residue is purified on column to yield 0.04 g product (34%). NMR (500 MHz): $^1$H: 1.34 (d, J=14.85 Hz, 9H), 3.88-3.95 (m, 1H), 3.95-4.02 (m, 1H), 4.05-4.10 (m, 1H), 4.10-4.16 (m, 1H), 6.85 (s, 1H), 7.34-7.40 (m, 1H), 7.43-7.48 (m, 2H), 7.48-7.52 (m, 1H), 7.60-7.66 (m, 1H), 7.84-7.90 (m, 3H). P$^{31}$:43.71. C$^{13}$:25.84, 34.27, 34.83, 65.46, 65.48, 99.66, 99.69, 127.87, 127.96, 128.20, 128.29, 128.98, 129.06, 131.35, 131.37, 131.65, 131.99, 132.08, 132.18, 132.25, 143.78, 143.83.

Example 10

Synthesis of 6j

A solution of 5b (7.0 g, 11.705 mmol) in anhydrous THF (60 ml) is cooled to −70° C. under argon atmosphere. And then freshly prepared FcLi (35.117 mmol) is added dropwise to the reaction mixture while maintaining temperature below −70° C. and stirred for 30 minutes at −70° C. After the starting material is consumed, the reaction is quenched using 30 ml of saturated ammonium chloride solution and extracted using 300 ml of ethyl acetate. The organic layer is dried over sodium sulphate and concentrated and purified on column to provide 6j (3.5 g, 67%) in 98.1:1.9 er. $^1$H NMR (400 MHz, CDCl$_3$) δ 3.69-3.75 (m, 1H), 3.84-3.95 (m, 2H), 3.99-4.01 (m, 1H), 4.05 (q, J=6.8 Hz, 1H), 4.26 (s, 5 H), 4.41-4.43 (m, 1H), 4.53-4.56 (m, 1H), 4.66-4.69 (m, 1H), 6.45 (s, 1H), 7.29-7.36 (m, 2H), 7.43-7.54 (m, 4H), 7.64-7.71 (m, 2H), 7.75 (dd, J=3.8, 7.9 Hz, 1H). $^{13}$C NMR (400 MHz, CDCl$_3$) δ 14.3, 65.3, 65.4, 69.9, 71.4 (d, J=10.9 Hz), 72.1, 72.2 (d, J=4.9 Hz), 72.4, 73.4 (d, J=13.9 Hz), 74.6, 77.4, 100.4 (d, J=4.8 Hz), 127.9 (d, J=9.7 Hz), 128.3 (d, J=12.3 Hz), 128.5 (d, J=12.5 Hz), 131.2 (d, J=10.2 Hz), 131.5 (d, J=2.8 Hz), 131.9 (d, J=2.6 Hz), 132.7, 133.2, 133.3, 133.7, 134.3, 135.4, 141.9 (d, J=7.2 Hz). $^{31}$P NMR (162 MHz, CDCl$_3$) δ 31.328. HPLC: Column: ChiralpackAD-3, 4.6×150 mm; IPA: Heptane (25:75), 1.0 ml/min, 220 nm, r$_t$=6.2 min, 11.0 min.

Examples 11 and 12

Scheme 10 below describes a method of making the compounds of then invention by reacting cyclic intermediate 2a with (2',6'-dimethoxybiphenyl-2-yl)magnesium bromide to provide the compound 5b followed by reaction with a lithium alkyl to provide a compound of the invention (denoted as compound 6).

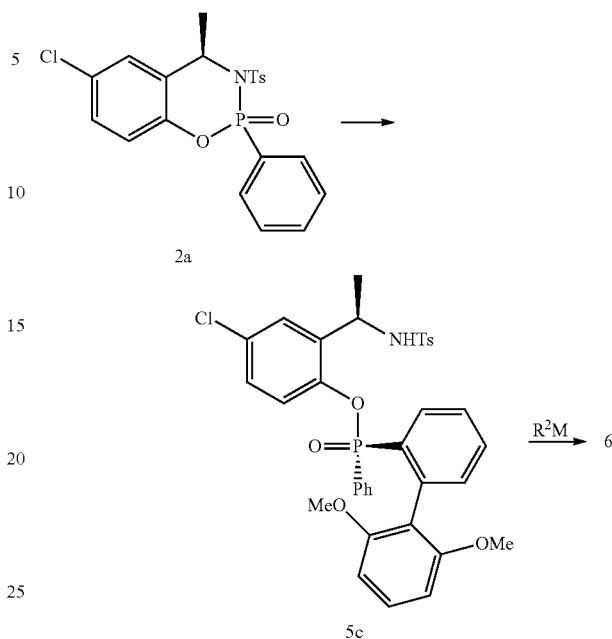

Specific compound of the invention prepared according to Scheme 10 are described in Table 5.

TABLE 5

Synthesis of chiral phosphine oxides 6k and 6l.

| Entry | R$^2$M | Product | ee | yield |
|---|---|---|---|---|
| Ex. 12 | CH$_3$MgCl | 6k | >99.9:0.1 | 61% |
| Ex. 13 | Fc—Li | 6l | 98.9:1.1 | 59% |

Example 12

Synthesis of 6k

A solution of (5c, 0.05 g, 0.075 mmol) in anhydrous THF (5 ml) is stirred at room temperature under argon atmosphere. Methyl magnesium chloride (0.12 ml, 0.377 mmol, 3.0 M in THF) is added dropwise to the reaction mixture and stirred at room temperature. The reaction is completed in 2 hours. The 2 ml of saturated ammonium chloride solution is added is quenched the reaction and extracted using 30 ml of ethyl acetate. The organic layer is dried over sodium sulphate and concentrated and purified on column to provide 6k (16 mg, 61% yield) in >99.9:0.1 er. $^1$H NMR (400 MHz, CDCl$_3$) δ 1.67 (d, J=13.7 Hz, 3H), 3.14 (s, 3H), 3.62 (s, 3H), 6.23 (d, J=8.5 Hz, 1H), 6.50 (d, J=8.5 Hz, 1H), 7.06-7.11 (m, 1H), 7.19-7.38 (m, 6H), 7.48-7.58 (m, 2H), 8.27-8.33 (m, 1H). $^{13}$C NMR (100 MHz, CDCl$_3$) δ 14.9, 15.7, 54.8, 55.3, 103.1 (d, J=37.6 Hz), 117.6, 127.2 (d, J=11.2 Hz), 127.7 (d, J=11.0 Hz), 129.8, 130.3 (d, J=9.9 Hz), 130.6 (d, J=2.7 Hz), 131.6 (d, J=2.6 Hz), 131.9 (d, J=10.6 Hz), 132.9, 133.1 (d, J=8.3 Hz), 133.9, 134.5, 135.5, 137.6 (d, J=9.5 Hz), 157.7 (d, J=14.6 Hz). $^{31}$P NMR (162 MHz, CDCl$_3$) δ 30.073. HPLC: Column: ChiralpackIA-3, 4.6×150 mm; IPA: Heptane (12:88), 1.5 ml/min, 220 nm, r$_t$=12.2 min, 15.2 min.

Example 12

Synthesis of 6l

A solution of (5c, 0.1 g, 0.151 mmol) in anhydrous THF (5 ml) is cooled to −78° C. under argon atmosphere. Then freshly prepared FcLi (85.1 mg, 0.453 mmol) is added dropwise to the reaction mixture and stirred at −78° C. The reaction is completed in 30 minutes. Then that the reaction is quenched using 2 ml of saturated ammonium chloride solution and extracted using 30 ml of ethyl acetate. The organic layer is dried over sodium sulphate and concentrated and purified to provide 6l (47 mg, 59% yield) in 98.9:1.1 er. $^1$H NMR (400 MHz, CDCl$_3$) δ 3.15 (s, 3H), 3.70 (s, 3H), 3.94 (s, 5H), 3.97-3.99 (m, 1H). 4.29-4.32 (m, 1H), 4.37-4.40 (m, 1H), 4.68-4.70 (m, 1H), 6.05 (d, J=8.0 Hz, 1H), 6.46 (d, J=8.4 Hz, 1H), 7.05-7.14 (m, 2H), 7.26-7.34 (m, 3H), 7.37-7.43 (m, 1H), 7.45-7.56 (m, 4H). $^{13}$C NMR (100 MHz, CDCl$_3$) δ 54.5, 55.7, 69.5, 70.8 (d, J=10.1 Hz), 71.3 (d, J=10.2 Hz), 71.6 (d, J=13.3 Hz), 73.1 (d, J=10.8 Hz), 73.6, 74.8, 102.2, 103.5, 126.3 (d, J=12.3 Hz), 127.2 (d, J=12.2 Hz), 129.2, 130.3 (d, J=2.8 Hz), 130.7 (d, J=9.9 Hz), 131.3 (d, J=2.5 Hz), 132.4 (d, J=10.1 Hz), 133.6 (d, J=11.0 Hz), 133.8, 133.9, 134.8, 135.0, 139.0 (d, J=8.3 Hz), 156.9, 158.3. $^{31}$P NMR (162 MHz, CDCl$_3$) δ 27.414. HPLC: Chiral AGP, 4.0×150 mm; mobile phase: A: pH5 buffer MB: ACN; isocratic: 79/21 A/B, 1.1 ml/min, 220 nm, r$_t$=4.0 min, 5.3 min.

Example 13

Synthesis of 6m

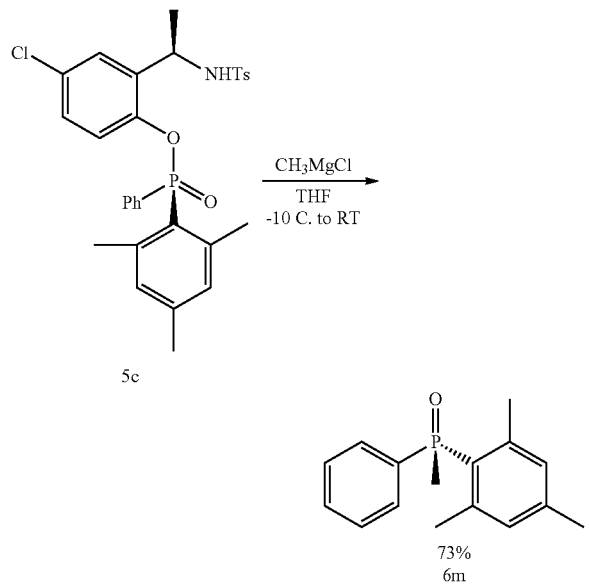

A solution of 5c (0.150 g, 0.265 mmol) in anhydrous THF (4 ml) is stirred under argon atmosphere at −10° C. temperature. Methyl magnesium chloride (0.35 ml, 1.06 mmol, 3.0 M in THF) is added dropwise to the reaction mixture and stirred for 15 minutes at −10 C, and then slowly warm to room temperature and stirred for 3-4 hrs. Once starting material is all consumed, the reaction is quenched using 2 ml of saturated ammonium chloride solution and then extracted using 30 ml of ethyl acetate. The organic layer is dried over sodium sulphate and concentrated, and purified on column to provide 6m (0.050 g, 73% yield) in 98.6:1.3 er. $^1$H NMR (400 MHz, CDCl$_3$) δ 2.10 (d, J=13.0 Hz, 3H), 2.29 (s, 3H), 2.40 (s, 6H), 7.39-7.48 (m, 3H), 7.56-7.63 (m, 2H), 6.88-6.91 (m, 2H); $^{13}$C NMR (100 MHz, CDCl$_3$) δ 19.9, 20.6, 21.0 (d, J=1.3 Hz), 125.4, 126.4, 128.8 (d, J=11.9 Hz), 129.5 (d, J=10.3 Hz), 131.1 (d, J=11.1 Hz), 131.2 (d, J=11.2 Hz), 136.9, 137.9, 141.6 (d, J=2.5 Hz), 142.7 (d, J=10.4 Hz). $^{31}$P NMR (162 MHz, CDCl$_3$) δ: 34.594 ppm. Chiral HPLC: ChiralpackAD-3, 4.6×150 mm; IPA: Heptane (25:75); 1.5 ml/min, 220 nm, r$_t$=3.0 min and 3.9 min.

Example 14

Synthesis of 6n

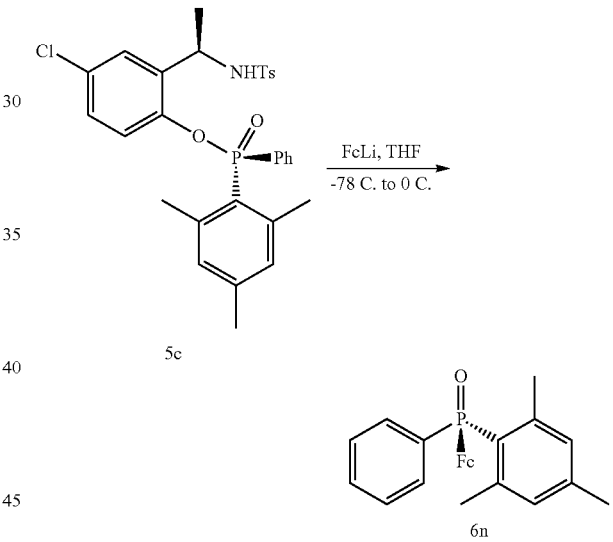

A solution of (5c, 0.2 g, 0.353 mmol) in anhydrous THF (5 ml) is cooled to −78° C. under argon atmosphere. A solution of FcLi (0.229 g, 1.23 mmol) is added to the reaction mixture and stirred for 1 hour at −78 C and then brought to 0° C. over 30 minutes. After the reaction completion, 2 ml of saturated ammonium chloride solution is added to quench the reaction and extracted using 30 ml of ethyl acetate. The organic layer is dried over sodium sulphate and concentrated, purified on column to provide 6n (87 mg, 58%) and 99:1 er. $^1$H NMR (400 MHz, CDCl$_3$) δ 2.16 (s, 6H), 2.24 (s, 3H), 3.97-4.0 (m, 1H), 4.27 (s, 5H), 4.36-4.39 (m, 1H), 4.50-4.52 (m, 1H), 4.69-4.72 (m, 1H), 6.79 (d, J=3.6 Hz, 2H), 7.43-7.52 (m, 3H), 7.70-7.76 (m, 2H). $^{13}$C NMR (100 MHz, CDCl$_3$) δ 20.9 (d, J=1.3 Hz), 24.0, 24.1, 71.0, 71.6, 71.8, 72.6, 72.8, 73.2, 73.4, 128.0, 128.2, 131.0 (d, J=10.1 Hz), 131.1 (d, J=10.2 Hz), 141.0 (d, J=2.5 Hz), 142.8 (d, J=10.4 Hz). $^{31}$P NMR (162 MHz, CDCl$_3$) δ: 30.108. Chiral HPLC: ChiralpackAD-3, 4.6×150 mm; IPA: Heptane (25:75); 1.5 ml/min, 220 nm, r$_t$=3.0 min and 3.9 min.

Example 15

Synthesis of 6o

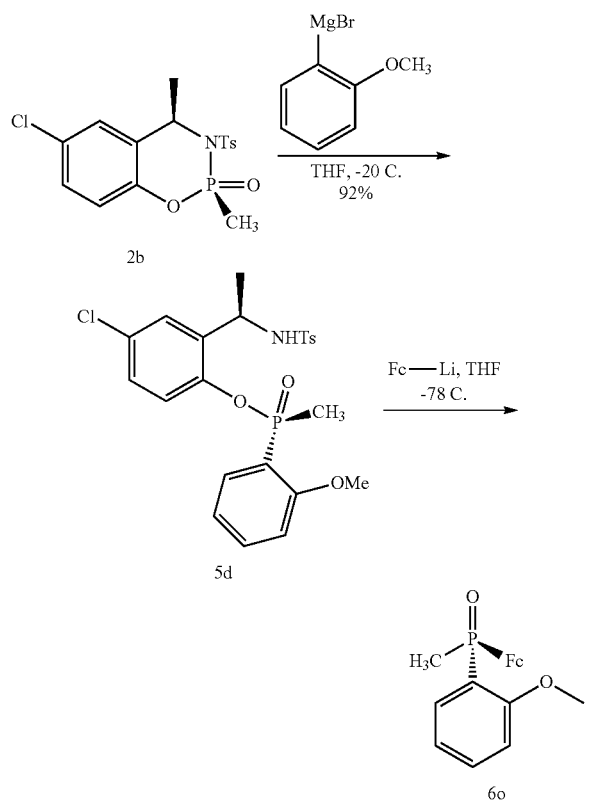

Step 1: Synthesis of 2b

A solution of (1, 2.0 g, 6.414 mmol) in anhydrous dichloromethane (20 ml) is cooled to −10° C. and then methyl phosphonic dichloride (1.01 g., 7.69 mmol), is added to the reaction mixture. And 1-methyl imidazole (1.0 ml, 16.053 mmol) is added to the reaction mixture over 10 minutes time while maintaining reaction temperature <−10° C. under argon atmosphere. The starting material is consumed in about 2 hours after addition of base and stirring the reaction mixture below <0° C. The reaction is quenched using 10 ml of water and extracted. Organic phase is washed with 10 ml of 1N HCl. The organic phase is then filtered through Celite and then concentrated. The residue is recrystallized using isopropanol: water to provide 2b (1.8 g, 75.6% yield) as a white solid. $^1$H NMR (400 MHz, CDCl$_3$) δ 2.07 (d, J=17.5 Hz, 3H), 2.42 (s, 3H), 4.43 (dd, J=10.6, 15.5 Hz, 1H), 4.67 (dd, J=10.6, 15.4 Hz, 1H), 7.03-7.09 (m, 1H), 7.28-7.34 (m, 2H), 8.01 (d, J=8.4 Hz, 2H). $^{13}$C NMR (100 MHz, CDCl$_3$) δ 15.5, 16.8, 21.8, 46.6, 120.4 (d, J=5.4 Hz), 126.1 (d, J=6.2 Hz), 127.1 (d, J=1.1 Hz), 128.3, 130.1, 130.2, 130.4, 135.2, 145.2, 147.6 (d, J=9.4 Hz). $^{31}$P NMR (162 MHz, CDCl$_3$) δ 24.5

Step 2: Synthesis of (R)-4-chloro-2-((S)-1-(4-methylphenylsulfonamido)ethyl)phenyl 2-methoxyphenyl (methyl)phosphinate (5d)

A solution of 2b (2.0 g, 5.19 mmol) in anhydrous THF (25 ml) is cooled to −20° C. under argon atmosphere. Then 2-methoxy phenyl magnesium bromide (5.71 ml, 5.71 mmol, 1.0 M in THF) is added dropwise to the reaction mixture and stirred for 2 hours at −20° C. After the starting material is consumed, the reaction is quenched using 20 ml of saturated ammonium chloride solution and extracted using 100 ml of ethyl acetate. The organic layer is dried over sodium sulphate and concentrated, and purified on column to provide 5d (2.4 g, 92%) in >99:5:0.5 dr. $^1$H NMR (400 MHz, CDCl$_3$) δ 1.3 (d, J=7.1 Hz, 3H), 1.98 (d, J=15.3 Hz, 3H), 2.27 (s, 3H), 4.04 (s, 3H), 4.56-4.66 (m, 1H), 6.07-6.25 (m, 1H), 6.83-6.88 (m, 1H), 6.94 (d, J=7.3 Hz, 2H), 7.02-7.15 (m, 3H), 7.36-7.41 (m, 2H), 7.61 (t, J=8.1 Hz, 1H), 8.0 (ddd, J=1.7, 7.4 Hz, 1H). $^{13}$C NMR (400 MHz, CDCl$_3$) δ 15.9, 16.9, 21.3, 22.3, 50.5, 50.6, 56.1, 111.3, 111.4, 117.1, 118.3, 121.0, 121.1, 126.8, 127.9, 128.4, 129.1, 133.9, 135.2, 135.5, 135.5, 137.5, 142.9, 146.9, 147.0, 160.3, 160.4. $^{31}$P NMR (162 MHz, CDCl$_3$) δ 42.044.

Step 3. Synthesis of 6o

A solution of (5d, 0.2 g, 0.405 mmol) in anhydrous THF (5 ml) is cooled to −78° C. under argon atmosphere. Then freshly prepared FcLi (230 mg, 1.21 mmol) is added dropwise to the reaction mixture and stirred at −78° C. The reaction is completed in 30 minutes. The reaction is quenched using 2 ml of saturated ammonium chloride solution and extracted using 30 ml of ethyl acetate. The organic layer is dried over sodium sulphate, concentrated, and purified on column to provide 6o (119 mg, 82%) in 98.8:1.2 er. $^1$H NMR (400 MHz, CDCl$_3$) δ 1.99 (d, J=13.8 Hz, 3H), 3.80 (s, 3H), 4.27 (s, 5H), 4.38 (s, 2H), 6.85-6.90 (m, 1H), 7.07 (t, J=7.5 Hz, 1H), 7.45 (t, J=8.1 Hz, 1H), 7.90-7.99 (m, 1H); $^{13}$C NMR (100 MHz, CDCl$_3$) δ 55.3, 69.6, 71.2, 71.9, 77.4, 110.8, 121.0 (d, J=9.7 Hz), 133.4, 133.6, 159.8. $^{31}$P NMR (162 MHz, CDCl$_3$) δ 29.246. HPLC: Chiralpack OJ_RH, 4.6×150 mm; 1% acetic acid in water, pH=4.5 adjusted with NH4OH; MB:ACN; isocratic: 45/55 A/B; 1.2 ml/min; 220 nm, r$_t$=2.1, 4.1 min.

Example 16

Synthesis of 6p

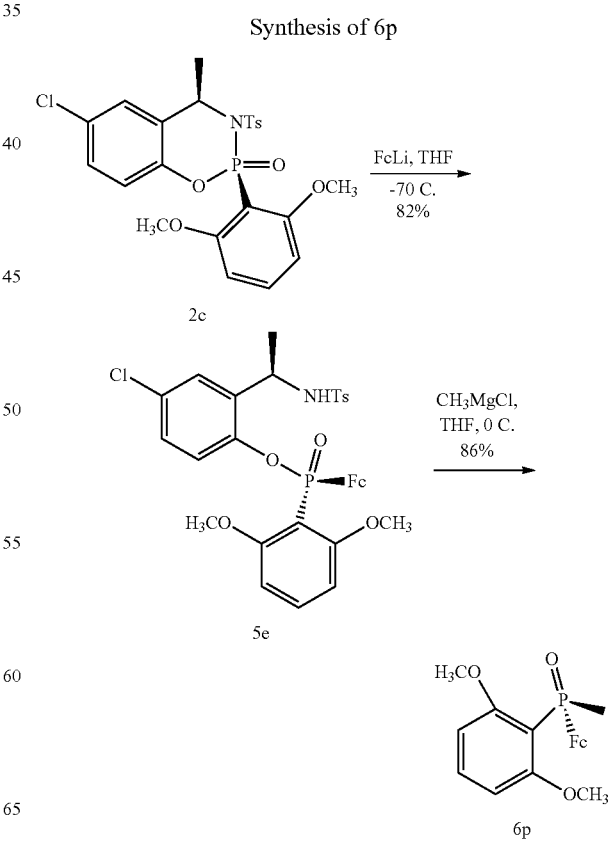

Step 1: Synthesis of 5e

A solution of 2c (0.5 g, 0.984 mmol) is dissolved in anhydrous THF (5 ml) cooled to −78° C. under argon atmosphere. Freshly prepared FcLi (223 mg, 1.18 mmol) is added dropwise to the reaction mixture and stirred at −78° C. The reaction is completed in 20 minutes. Then the reaction is quenched using 2 ml of saturated ammonium chloride solution and extracted using 30 ml of ethyl acetate. The organic layer is dried over sodium sulphate, concentrated, and purified on column to provide 5e (560 mg, 82% yield). $^1$H NMR (400 MHz, CDCl$_3$) δ 1.55 (d, J=6.9 Hz, 3H), 2.27 (s, 3H), 3.81 (s, 6H), 4.32 (s, 5H), 4.43-4.51 (m, 3H), 4.61 (bs, 1H), 4.78 (bs, 1H), 5.99 (d, J=9.6 Hz, 1H), 6.50 (d, J=2.7 Hz, 1H), 6.62 (dd, J=5.1, 8.6 Hz, 2H), 6.87-6.92 (m, 3H), 7.24-7.28 (m, 2H), 7.45 (t, J=8.4 Hz, 1H). 7.68 (d, J=8.9 Hz, 1H). $^{13}$C NMR (100 MHz, CDCl$_3$) δ 14.4, 21.2, 21.5, 22.5, 52.2, 56.7, 60.6, 70.2, 71.0 (d, J=12.2 Hz), 71.4 (d, J=13.8 Hz), 72.1 (d, J=19 Hz), 72.5 (d, J=12.2 Hz), 73.1, 74.7, 105.4 (d, J=7.4 Hz), 107.0, 108.4, 121.3 (d, J=4.3 Hz), 127.0, 127.9, 128.2, 128.6, 129.3, 132.8 (d, J=7.3 Hz), 135.3, 137.5, 143.1, 148.5 (d, J=7.9 Hz), 163.4 (d, J=1.6 Hz). $^{31}$P NMR (162 MHz, CDCl$_3$) δ 33.346.

Step 2: Synthesis of 6p

A solution of 5e (0.1 g, 0.144 mmol) in anhydrous THF (5 ml) is cooled to 0° C. under argon atmosphere. Methyl magnesium chloride (0.25 ml, 0.722 mmol, 3.0 M in THF) is added dropwise to the reaction mixture and stirred for 3 hrs at 0° C. After the completion of the reaction, 1 ml of saturated ammonium chloride solution is added to quench the reaction and extracted using 30 ml of ethyl acetate. The organic layer is dried over sodium sulphate and concentrated, and purified on column to provide 6p (47 mg, 86% yield) in 99:1 er. $^1$H NMR (400 MHz, CDCl$_3$) δ 2.10 (d, J=14.3 Hz, 3H), 3.71 (s, 6H), 4.25-4.27 (m, 1H), 4.30 (s, 5H), 4.31-4.33 (m, 1H), 4.36-4.38 (m, 1H), 4.69-4.71 (m, 1H), 6.48 (dd, J=4.1, 8.5 Hz, 2H), 7.29 (t, J=8.5 Hz, 1H). $^{13}$C NMR (100 MHz, CDCl$_3$) δ 20.1, 20.9, 55.8, 69.7, 70.2, 70.4 (d, J=5.2 Hz), 70.5, 70.8, 71.0, 78.1, 79.3, 104.7 (d, J=6.2 Hz), 111.1, 112.1, 133.5, 162.3. $^{31}$P (162 MHz, CDCl$_3$) δ 28.745. HPLC: Column: ChiralpackAD-H, 4.6×250 mm; IPA: Heptane (2:98), 1.0 ml/min, 220 nm, r$_t$=11.1 min, 12.1 min.

Example 17

Synthesis 6q

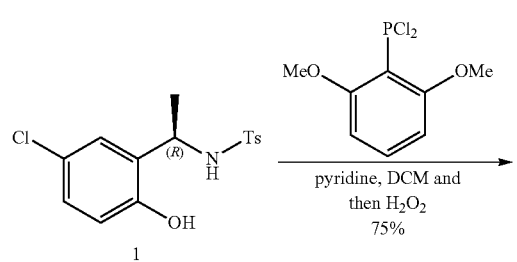

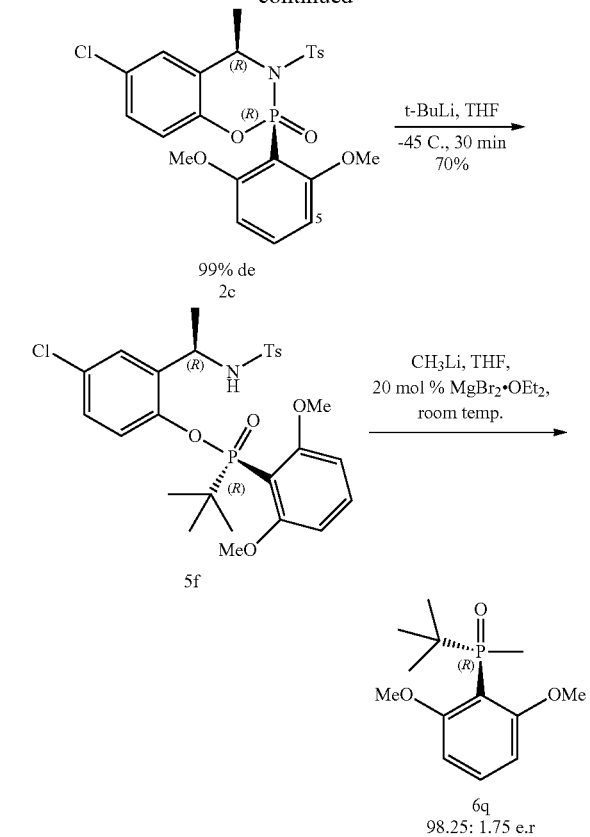

Step 1: Synthesis of 5f

A solution of 2c (1.0 g, 1.97 mmol) in anhydrous THF (30 ml) is heated to 45° C. to dissolve the compound and cooled to −45° C. under argon atmosphere. t-BuLi (2.5 ml, 3.94 mmol, 1.6 M in pentane) is added dropwise to the reaction mixture and stirred for 30 minutes at −45° C. After the starting material is consumed, the reaction is quenched using 10 ml of saturated ammonium chloride solution, extracted using 50 ml of ethyl acetate, and dried over sodium sulphate. The organic solvent is removed and residue purified on column to provide 5f (0.770 g, 70%) in >99:1 dr. $^1$H NMR (400 MHz, CDCl$_3$) δ 1.3 (d, J=17.4 Hz, 9H), 1.44 (d, J=6.9 Hz, 3H), 2.31 (s, 3H), 3.66 (s, 6H), 4.89-4.98 (m, 1H), 5.74 (d, J=7.7 Hz, 1H), 6.53-6.59 (m, 2H), 6.77-6.82 (m, 1H), 6.95-6.98 (m, 1H), 7.04 (d, J=8.9 Hz, 1H), 7.12 (d, J=8.1 Hz, 2H), 7.44 (t, J=8.3 Hz, 1H), 7.60 (d, J=8.2 Hz, 2H). $^{13}$C NMR (100 MHz, CDCl$_3$) δ 21.3, 22.9, 24.4, 34.8, 35.9, 48.7, 56.0, 104.6 (d, J=7.0 Hz), 119.0 (d, J=5.5 Hz), 126.8, 126.9, 127.4, 127.8, 129.5, 133.0 (d, J=6.8 Hz), 135.1, 137.2, 143.1, 147.8 (d, J=9.8 Hz), 163.4 (d, J=1.8 Hz). $^{31}$P NMR (162 MHz, CDCl$_3$) δ 48.419.

Step 2: Synthesis of 6q

A solution of 5f (0.70 g, 1.23 mmol) in anhydrous THF (10 ml) is added MgBr2.OEt2 (0.063 g, 0.247 mmol) and stirred at rt for about 30 minutes. Then methyl lithium (2.70 ml, 4.32 mmol, 1.6 M in pentane) is added dropwise to the reaction mixture and stirred for 30 minutes at rt. After the starting material is consumed, the reaction is quenched using 5 ml of saturated ammonium chloride solution and extracted using 50 ml of ethyl acetate. The organic layer is dried over sodium sulphate, concentrated, and purified on column to provide 6p (0.2 g, 63%) in 98.2:1.7 er. $^1$H NMR (400 MHz, CDCl$_3$) δ

1.15 (d, J=15.5 Hz, 9H), 1.80 (d, J=13.2 Hz, 3H), 3.81 (s, 6H), 6.57 (dd, J=3.8, 8.3 Hz, 2H), 7.38 (t, J=8.3 Hz, 1H). $^{13}$C NMR (100 MHz, CDCl$_3$) δ 15.6, 16.3, 24.5 (d, J=1.6 Hz), 34.3, 35.0, 55.7, 104.5 (d, J=5.9 Hz), 103.6, 163.2. $^{31}$P NMR (162 MHz, CDCl$_3$) δ 51.210;

Scheme 11 below describes an alternative method of making the compounds of the invention (denoted as compound 6) by reacting compounds of formula (IIa) with organometallic reagents.

Scheme 11

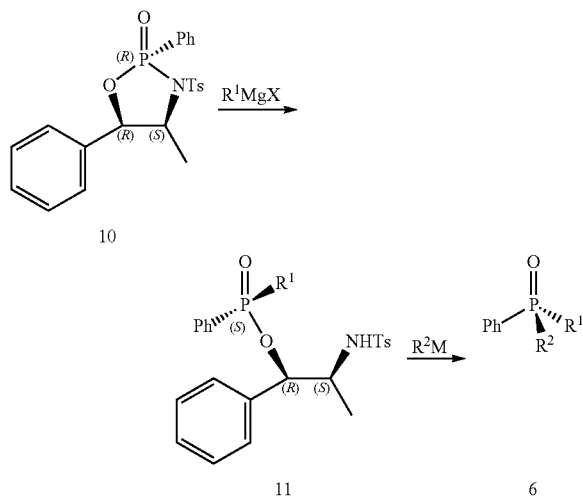

Synthesis of 10

A solution of (1R, 2S)—N-tosyl-norephedrine (120 g) in CH2C12 (800 mL) is cooled to −20° C. and then PhP(O)Cl$_2$ (1.3 eq) is added, followed by 1-Me-imidazole (2.5 eq), and the mixture is stirred and slowly warmed to room temperature and stirred overnight. After the completion of the reaction, the mixture is filtered to remove the solid. Then the organic phase is washed with brine, aqueous NaHCO3 solution, and 1 N HCl (150 mL). The to organic phase is dried and concentrated. The residue is recrystallized from ethyl acetate/hexane (1:2, v/v) twice to provide 10 (125 g) in 75% yields.

Synthesis of (R)-((1R,2S)-2-(4-methylphenylsulfonamido)-1-phenylpropyl) 2-methoxyphenyl(phenyl)phosphinate (11a)

A solution of 10 (2.0 g, 5.12 mmol) in anhydrous THF (40 ml) is cooled to −40° C. under argon atmosphere. Then 2-methoxy phenyl magnesium bromide (6.15 ml, 6.15 mmol, 1.0 M in THF) is added dropwise to the reaction mixture. During addition, the temperature rises to about −30° C. The mixture is stirred for 1 hour at −30° C., quenched using 5 ml of saturated ammonium chloride solution, and extracted using 100 ml of ethyl acetate. The organic layer is dried over sodium sulphate and concentrated. The residue is purified on A silica column to provide 11a (2.2 g, 91%) in optically pure form. $^1$H NMR (400 MHz, CDCl$_3$) δ 1.08 (d, J=6.8 Hz, 3H), 2.31 (s, 3H), 3.52-3.61 (m, 1H), 3.77 (s, 3H), 4.85 (d, J=9.4 Hz, 1H), 6.93-6.99 (m, 1H), 7.06-7.15 (m, 5H), 7.21-7.35 (m,

TABLE 6

Synthesis of chiral phosphine oxides from 1,2-amino alcohol templates.

| Entry | R$^1$M | yield (11) | R$^2$M | Product | er | yield |
|---|---|---|---|---|---|---|
| Ex. 18 | 2-MeO-C$_6$H$_4$-MgBr | 91% (11a) | MeMgBr | 6a | 99:1 | 38% |
| Ex. 19 | | | MeLi | | 90:10 | 70% |
| Ex. 20 | | | tBuLi | 6b | 98:2 | 51% |
| Ex. 21 | mesityl-MgBr | 47% (11b) | MeLi | 6m | 93:7 | 55% |
| Ex. 22 | tBuLi (4) tBuMgCl | 62% (11c) | MeMgBr MeLi | 6r | no reaction nd | 42% |

6H), 7.43-7.49 (m, 1H), 7.54-7.60 (m, 1H), 7.63-7.72 (m, 4H), 7.95-8.02 (m, 1H). $^{13}$C NMR (100 MHz, CDCl$_3$) δ 14.4, 21.4, 54.9 (d, J=2.5 Hz), 55.5, 80.4 (d, J=5.9 Hz), 111.7 (d, J=8.0 Hz), 118.1, 119.5, 120.9 (d, J=12.9 Hz), 125.5, 127.0, 127.8, 128.0, 128.1, 128.3, 129.4, 129.7, 131.4, 132.0, 132.1 (d, J=3.1 Hz), 134.4 (d, J=6.7 Hz), 134.9 (d, J=1.9 Hz), 138.0 (d, J=5.6 Hz), 138.5, 142.7, 160.7 (d, J=4.2 Hz). $^{31}$P NMR (162 MHz, CDCl$_3$) δ 33.648.

Synthesis of 11b

Step 1. Synthesis of 11b: A solution of 10 (2.0 g, 4.68 mmol) in anhydrous THF (30 ml) is stirred at room temperature under argon atmosphere. Then 2-mesityl magnesium bromide (7.0 ml, 7.02 mmol, 1.0 M in THF) is added dropwise to the reaction mixture. After stirring at room temperature for about 1 hour, the reaction is quenched using 10 ml of saturated ammonium chloride solution and extracted using 100 ml of ethyl acetate. The organic layer is dried over sodium sulphate, concentrated, and the residue is purified on silica column to provide 11b (1.2 g, 47%) in optically pure form. $^1$H NMR (400 MHz, CDCl$_3$) δ 1.10 (d, J=6.8 Hz, 3H), 2.34 (s, 3H), 2.4 (s, 3H), 2.5 (s, 6H), 3.51-3.65 (m, 1H), 5.18 (dd, J=1.8, 10.3 Hz), 6.92 (d, J=4.3 Hz, 1H), 6.96-6.98 (m, 2H), 7.16-7.25 (m, 8H), 7.37-7.47 (m, 3H), 7.81 (d, J=8.3 Hz, 2H) $^{13}$C NMR (100 MHz, CDCl$_3$) δ 15.1, 21.1 (d, J=1.2 Hz), 21.5, 54.8 (d, J=1.3 Hz), 81.6 (d, J=6.1 Hz), 123.3, 124.7, 126.1, 127.2, 128.0, 128.2, 128.3, 128.4, 130.9 (d, J=4.5 Hz), 131.0 (d, J=1.8 Hz), 131.8 (d, J=3.0 Hz), 132.2, 133.5, 137.7 (d, J=6.2 Hz), 138.5, 142.5 (d, J=3.0 Hz), 142.8, 142.9, 143.0. $^{31}$P NMR (162 MHz, CDCl$_3$) δ 40.844.

Synthesis of 11c:

A solution of 10 (1 g, 2.34 mmol) in anhydrous THF (15 ml) is cooled to −70° C. under argon atmosphere. And t-BuLi (1.60 ml, 2.57 mmol, 1.6 M in pentane) is added dropwise to the reaction mixture and stirred for 30 minutes at −70° C. After the reaction completion, the reaction is quenched using 5 ml of saturated ammonium chloride solution and extracted using 50 ml of ethyl acetate. The organic layer is dried over sodium sulphate, concentrated, and the residue is purified on silica column to provide 11c (0.68 g, 62%) in optically pure form. $^1$H NMR (400 MHz, CDCl$_3$) δ 1.08 (d, J=6.9 Hz, 3H), 1.22 (d, J=16.1 Hz, 9H), 2.24 (s, 3H), 3.47-3.55 (m, 1H), 4.61 (d, J=8.9 Hz, 1H), 6.98-7.05 (m, 4H), 7.28-7.36 (m, 5H), 7.43-7.55 (m, 3H), 7.74 (d, J=8.2 Hz, 2H), 7.82 (d, J=9.6 Hz, 1H). $^{13}$C NMR (100 MHz, CDCl$_3$) δ 14.0, 21.4, 24.3, 32.4, 33.4, 55.0, 80.9 (d, J=8.2 Hz), 125.2, 125.3, 126.5, 127.0, 128.1, 128.3, 126.5, 127.0, 128.1, 128.3, 128.4, 128.6, 129.3, 132.5 (d, J=2.8 Hz), 133.3 (d, J=7.1 Hz), 133.3 (d, J=9.3 Hz), 138.2 (d, J=7.1 Hz), 138.7, 142.5. $^{31}$P NMR (162 MHz, CDCl$_3$) δ 56.157.

Example 18

Synthesis of 6a from 11a with MeMgCl

A solution of 11a (0.5 g, 0.936 mmol) in anhydrous THF (10 ml) is stirred under argon atmosphere at room temperature. And then methylmagnesium chloride (1.87 ml, 5.61 mmol, 3.0 M in THF) is added dropwise to the reaction mixture and stirred for 8 hours at room temperature. The reaction mixture is quenched using 2 ml of saturated ammonium chloride solution and extracted using 50 ml of ethyl acetate. The organic layer is dried over sodium sulphate, concentrated, and purified on column to provide 6a (90 mg, 38% yield) in 99:1 er.

Example 19

Synthesis of 6a from 11a with MeLi

A solution of 11a (0.2 g, 385 mmol) in anhydrous THF (5 ml) is stirred under argon atmosphere at −78° C. temperature. Methyl lithium (1.0 ml, 1.54 mmol, 1.6 M in Et$_2$O) is added dropwise to the reaction mixture and stirred for 15 minutes at −78 C. The reaction is quenched using 2 ml of saturated ammonium chloride solution and extracted using 30 ml of ethyl acetate. The organic layer is dried over sodium sulphate, concentrated, and purified on column to provide 6a (58 mg, 55% yield) in 85:15 er.

Example 20

Synthesis of 6b from 11a

A solution of 11a (0.2 g, 385 mmol) in anhydrous THF (5 ml) is stirred under argon atmosphere at −78° C. temperature. Then t-butyllithium (1.0 ml, 1.54 mmol, 1.6 M in Pentane) is added dropwise to the reaction mixture and stirred for 15 minutes at −78 C. The reaction is quenched using 2 ml of saturated ammonium chloride solution and extracted using 30 ml of ethyl acetate. The organic layer is dried over sodium sulphate, concentrated, and purified on column to provide 6b (58 mg, 51% yield) in 98:2 er.

Example 21

Synthesis of 6m from 11b

Procedure: A solution of 11b (0.1 g, 0.182 mmol) in anhydrous THF (5 ml) is stirred under argon atmosphere at −30° C. temperature. Methyl lithium (1.0 ml, 0.639 mmol, 1.6 M in Et$_2$O) is added dropwise to the reaction mixture and stirred for 15 minutes at −30 C. The reaction is quenched using 2 ml of saturated ammonium chloride solution and extracted using 30 ml of ethyl acetate. The organic layer is dried over sodium sulphate, concentrated, and purified on silica column to provide 6m (26 mg, 55% yield) in 93:7 er. $^1$H NMR (400 MHz, CDCl$_3$) δ 2.10 (d, J=13.0 Hz, 3H), 2.29 (s, 3H), 2.40 (s, 6H), 7.39-7.48 (m, 3H), 7.56-7.63 (m, 2H), 6.88-6.91 (m, 2H). $^{13}$C NMR (100 MHz, CDCl$_3$) δ 14.1, 14.8, 19.8, 20.5, 21.0, 23.5, 23.6, 127.6, 127.7, 128.3, 128.4, 128.6, 128.7, 129.4, 129.5, 130.4, 130.5, 131.0, 131.2, 131.3, 141.5, 142.6, 142.7. $^{31}$P NMR (162 MHz, CDCl$_3$) δ: 34.778. Chiral HPLC: ChiralpackAD-3, 4.6×150 mm; IPA: Heptane (25:75); 1.5 ml/min, 220 nm, r$_t$=3.3 min and 4.3 min.

Example 22

Synthesis of 6r from 11c

A solution of 11c (0.2 g, 0.412 mmol) in anhydrous THF (5 ml) is stirred under argon atmosphere at −10° C. temperature. Methyl lithium (0.77 ml, 1.23 mmol, 1.6 M in Et$_2$O) is added dropwise to the reaction mixture and stirred for 15 minutes at −10 C. The reaction is quenched using 2 ml of saturated ammonium chloride solution and extracted using 30 ml of ethyl acetate. The organic layer is dried over sodium sulphate, concentrated, and purified on column to provide 6r (35 mg, 43% yield). $^1$H NMR (400 MHz, CDCl$_3$) δ 1.13 (d, J=14.9

Hz, 9H), 1.73 (d, J=12.1 Hz, 3H), 7.44-7.59 (m, 3H), 7.69-7.75 (m, 3H). $^{31}$P NMR (162 MHz, CDCl$_3$) δ: 47.623.

What is claimed is:

1. A method of making a compound of formula (I):

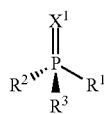
(I)

the method comprising allowing a compound of formula (IIa) or (IIb):

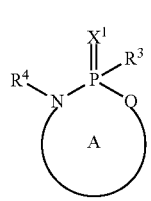
(IIa)

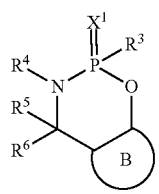
(IIb)

to react with a first organometallic reagent of formula M$^1$-R$^1$ followed by reaction with a second organometallic reagent of formula M$^2$-R$^2$ to provide the compound of formula (I);

wherein ring A of the compound of formula (IIa) represents a 5- to 7-membered heterocyclic ring optionally substituted by 1 to 3 substituents independently selected from halogen, hydroxyl, —(C$_1$-C$_6$)alkyl, —O(C$_1$-C$_6$)alkyl, —CF$_3$, —(C$_6$-C$_{10}$)aryl, and -(5 to 11-membered)heteroaryl;

ring B of the compound of formula (IIb) represents a (C$_6$-C$_{10}$)aryl or a (5 to 11-membered)heteroaryl; wherein each of said (C$_6$-C$_{10}$)aryl and (5 to 11-membered)heteroaryl of said B ring is optionally substituted by 1 to 3 substituents independently selected from halogen, hydroxyl, —(C$_1$-C$_6$)alkyl, —O(C$_1$-C$_6$)alkyl, and —CF$_3$;

R$^1$, R$^2$ and R$^3$ represent different groups, wherein;

R$^1$ is selected from —(C$_1$-C$_6$)alkyl, —(C$_6$-C$_{10}$)aryl, and -(5 to 11-membered)heteroaryl; wherein each of said —(C$_1$-C$_6$)alkyl, —(C$_6$-C$_{10}$)aryl, and -(5 to 11-membered)heteroaryl of said R$^1$ group is optionally substituted by 1 to 3 substituents independently selected from halogen, hydroxyl, —(C$_1$-C$_6$)alkyl, —O(C$_1$-C$_6$)alkyl, —CF$_3$, dioxolanyl, and phenyl optionally substituted with 1 to 3 R$^7$ groups;

each R$^2$ is independently selected from hydrogen, —(C$_1$-C$_6$)alkyl, —(C$_2$-C$_6$)alkenyl, —(C$_2$-C$_6$)alkynyl, —(C$_3$-C$_6$)cycloalkyl, -(5 to 11-membered)heterocyclyl, —(C$_6$-C$_{10}$)aryl, -(5 to 11-membered)heteroaryl, —N(R$^{2a}$)$_2$, and ferrocenyl; wherein each of said —(C$_1$-C$_6$)alkyl, —(C$_2$-C$_6$)alkenyl, —(C$_2$-C$_6$)alkynyl, —(C$_3$-C$_6$)cycloalkyl, -(5 to 11-membered)heterocyclyl, —(C$_6$-C$_{10}$)aryl, and -(5 to 11-membered)heteroaryl of said R$^2$ group is optionally substituted by 1 to 3 substituents independently selected from halogen, hydroxyl, —(C$_1$-C$_6$)alkyl, —O(C$_1$-C$_6$)alkyl, —CF$_3$, and phenyl optionally substituted with 1 to 3 R$^8$ groups;

R$^3$ is selected from —(C$_6$-C$_{10}$)aryl, and -(5 to 11-membered)heteroaryl; wherein each of said —(C$_6$-C$_{10}$)aryl, and -(5 to 11-membered)heteroaryl of said R$^3$ group is optionally substituted by 1 to 3 substituents independently selected from halogen, hydroxyl, —(C$_1$-C$_6$)alkyl, —O(C$_1$-C$_6$)alkyl, and —CF$_3$, and phenyl optionally substituted with 1 to 3 R$^9$ groups;

R$^4$ is selected from (C$_1$-C$_6$)alkyl, —(C$_3$-C$_6$)cycloalkyl, -(5 to 11-membered)heterocyclyl, —(C$_6$-C$_{10}$)aryl, and -(5 to 11-membered)heteroaryl; wherein each of said —(C$_1$-C$_6$)alkyl, —(C$_2$-C$_6$)alkenyl, —(C$_2$-C$_6$)alkynyl, —(C$_3$-C$_6$)cycloalkyl, -(5 to 11-membered)heterocyclyl, —(C$_6$-C$_{10}$)aryl, and -(5 to 11-membered)heteroaryl of said R$^4$ group is optionally substituted by 1 to 3 substituents independently selected from halogen, hydroxyl, —(C$_1$-C$_6$)alkyl, —O(C$_1$-C$_6$)alkyl, —CF$_3$, and phenyl or R$^4$ is selected from phenylsulfonyl, pyridinylsulfonyl, and pyrimidinylsulfonyl; wherein each of said phenylsulfonyl, pyridinylsulfonyl, and pyrimidinylsulfonyl of said R$^4$ group is optionally substituted by 1 to 3 substituents independently selected from halogen, hydroxyl, —(C$_1$-C$_6$)alkyl, —O(C$_1$-C$_6$)alkyl, and —CF$_3$;

R$^5$ and R$^6$ are each independently selected from hydrogen, —(C$_1$-C$_6$)alkyl, —CF$_3$, —(C$_3$-C$_6$)cycloalkyl, -(5 to 11-membered)heterocyclyl, —(C$_6$-C$_{10}$)aryl, and -(5 to 11-membered)heteroaryl; wherein each of said —(C$_1$-C$_6$)alkyl, —(C$_3$-C$_6$)cycloalkyl, -(5 to 11-membered)heterocyclyl, —(C$_6$-C$_{10}$)aryl, and -(5 to 11-membered)heteroaryl of said R$^5$ and R$^6$ of said R$^5$ and R$^6$ groups is optionally substituted by 1 to 3 substituents independently selected from halogen, hydroxyl, —(C$_1$-C$_6$)alkyl, —O(C$_1$-C$_6$)alkyl, and —CF$_3$;

R$^7$, R$^8$ and R$^9$ are each independently selected from —(C$_1$-C$_6$)alkyl, —CF$_3$, —(C$_3$-C$_6$)cycloalkyl, -(5 to 11-membered)heterocyclyl, —(C$_6$-C$_{10}$)aryl, and -(5 to 11-membered)heteroaryl; wherein each of said —(C$_1$-C$_6$)alkyl, —(C$_3$-C$_6$)cycloalkyl, -(5 to 11-membered)heterocyclyl, —(C$_6$-C$_{10}$)aryl, and -(5 to 11-membered)heteroaryl of said R$^7$, R$^8$ and R$^9$ groups are each independently substituted by 1 to 3 groups selected from halogen, hydroxyl, —(C$_1$-C$_6$)alkyl, —O(C$_1$-C$_6$)alkyl, —CF$_3$, and 1,3-dioxolanyl;

X$^1$ is selected from O, S, BH$_3$ or an electron pair;

M$^1$ and M$^2$ are each independently Li, MgX$^2$ or ZnX$^2$;

X$^2$ is selected from F, Cl, Br, and I; and j is 0, 1 or 2.

2. The method of claim 1, wherein X$^1$ is O.

3. The method of claim 1, wherein X$^1$ is an electron pair.

4. The method of claim 1, wherein R$^3$ is phenyl.

5. The method of claim 1, wherein R$^1$ is —(C$_6$-C$_{10}$)aryl; wherein said —(C$_6$-C$_{10}$)aryl is substituted by 1 to 3 substituents independently selected —(C$_1$-C$_6$)alkyl, —O(C$_1$-C$_6$)alkyl, dioxolanyl, and 1,3-dimethoxyphenyl.

6. The method of claim 1, wherein R$^1$ is —(C$_1$-C$_6$)alkyl.

7. The method of claim 1, wherein R$^2$ is —(C$_1$-C$_6$)alkyl.

8. The method of claim 1, wherein R$^2$ is selected from methyl and t-butyl.

9. The method of claim 1, wherein R$^2$ is ferrocenyl.

10. The method of claim 1, wherein R$^2$ is selected from —(C$_2$-C$_6$)alkenyl and —(C$_2$-C$_6$)alkynyl substituted by phenyl.

11. The method of claim 1, wherein $R^2$ is selected from phenyl substituted by 1,3-dimethoxyphenyl.

12. The method of claim 1, wherein $R^4$ is selected from phenylsulfonyl, pyridinylsulfonyl, and pyrimidinylsulfonyl; wherein each of said phenylsulfonyl, pyridinylsulfonyl, and pyrimidinylsulfonyl is optionally substituted by 1 to 3 substituents independently selected from halogen, hydroxyl, —$(C_1-C_6)$alkyl, —$O(C_1-C_6)$alkyl, and —$CF_3$.

13. The method of claim 1, wherein the compound of formula (IIa) is reacted with the first organometallic reagent of formula $M^1$-$R^1$ followed by reaction with the second organometallic reagent of formula $M^2$-$R^2$ to provide the compound of formula (I).

14. The method of claim 13, wherein the compound of formula (IIa) is a five-membered heterocyclic ring of formula:

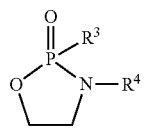

wherein said five-membered heterocyclic ring is optionally substituted by 1 to 3 substituents independently selected from halogen, hydroxyl, —$(C_1-C_6)$alkyl, —$O(C_1-C_6)$alkyl, —$CF_3$, —$(C_6-C_{10})$aryl, and -(5 to 11-membered) heteroaryl, including diastereomers and enantiomers thereof.

15. The method of claim 13, wherein the compound of formula (IIa) is a five-membered heterocyclic ring of structure:

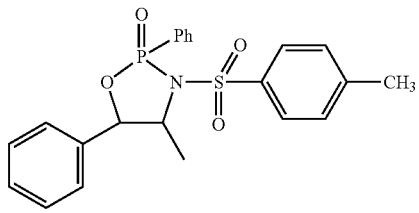 [SMILES: Cc1ccc(S(=O)(=O)N2C(C)C(c3ccccc3)OP2(=O)c2ccccc2)cc1]

including diastereomers and enantiomers thereof.

16. The method of claim 13, wherein the compound of formula (IIa) is a five-membered heterocyclic ring of structure:

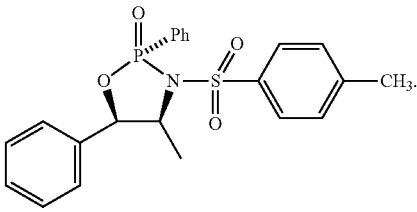 [SMILES: Cc1ccc(S(=O)(=O)N2[C@@H](C)[C@@H](c3ccccc3)O[P@]2(=O)c2ccccc2)cc1]

17. The method of claim 1, wherein the compound of formula (IIb) is reacted with the first organometallic reagent of formula $M^1$-$R^1$ followed by reaction with the second organometallic reagent of formula $M^2$-$R^2$ to provide the compound of formula (I).

18. The method of claim 17, wherein ring B of the compound of formula (IIb) is a —$(C_6-C_{10})$aryl optionally substituted by 1 to 3 substituents independently selected from halogen, hydroxyl, —$(C_1-C_6)$alkyl, —$O(C_1-C_6)$alkyl, and —$CF_3$.

19. The method of claim 17, wherein ring B of the compound of formula (IIb) is a $C_6$-aryl substituted by halo.

20. The method of claim 17, wherein the compound of formula (IIb) is:

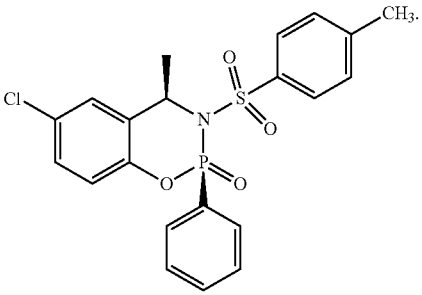 [SMILES: Cc1ccc(S(=O)(=O)N2[C@H](C)c3cc(Cl)ccc3O[P@]2(=O)c2ccccc2)cc1]

* * * * *